(12) United States Patent
Chen et al.

(10) Patent No.: US 11,413,335 B2
(45) Date of Patent: Aug. 16, 2022

(54) HEMOSTATIC COMPOSITIONS AND METHODS OF MAKING THEREOF

(71) Applicants: GUANGZHOU BIOSEAL BIOTECH CO. LTD., Guangzhou Science (CN); Ethicon, Inc., Somerville, NJ (US)

(72) Inventors: Shuang Chen, Guangzhou (CN); Yufu Li, Somerville, NJ (US); Aibin Yu, Shenzhen (CN); Jianping Yu, Guangzhou (CN)

(73) Assignees: Guangzhou Bioseal Biotech Co. Ltd, Guangzhou Science (CN); Ethicon, Inc., Raritan, NJ (US)

( * ) Notice: Subject to any disclaimer, the term of this patent is extended or adjusted under 35 U.S.C. 154(b) by 0 days.

(21) Appl. No.: 15/895,468

(22) Filed: Feb. 13, 2018

(65) Prior Publication Data
US 2019/0247474 A1 Aug. 15, 2019

(51) Int. Cl.
| | | |
|---|---|---|
| A61K 38/36 | (2006.01) | |
| A61K 38/48 | (2006.01) | |
| A61K 31/717 | (2006.01) | |
| A61K 9/16 | (2006.01) | |
| A61P 11/00 | (2006.01) | |
| A61K 9/00 | (2006.01) | |
| A61K 9/06 | (2006.01) | |
| A61L 24/10 | (2006.01) | |
| A61L 24/08 | (2006.01) | |

(52) U.S. Cl.
CPC .......... *A61K 38/4833* (2013.01); *A61K 9/007* (2013.01); *A61K 9/06* (2013.01); *A61K 9/16* (2013.01); *A61K 9/1611* (2013.01); *A61K 9/1617* (2013.01); *A61K 9/1682* (2013.01); *A61K 31/717* (2013.01); *A61K 38/363* (2013.01); *A61L 24/08* (2013.01); *A61L 24/106* (2013.01); *A61L 24/108* (2013.01); *A61P 11/00* (2018.01); *A61L 2400/04* (2013.01)

(58) Field of Classification Search
CPC ............. A61K 9/1688; A61K 38/4833; A61K 9/1611; A61K 9/1682; A61K 9/06; A61K 9/16; A61K 9/1617; A61K 31/717; A61K 38/363; A61K 9/007; A61K 35/16; A61K 9/0026; A61K 9/1658; A61K 9/1676; A61F 13/00063; A61F 2013/00306; A61F 2013/00472; A61F 2013/00927; A61L 26/0047; A61L 26/0057; A61L 26/0076; A61L 27/54; A61L 2300/00; A61L 2300/20; A61L 2300/252; A61L 2300/802; A61L 2400/04; A61L 24/08; A61L 24/106; A61L 24/108; A61P 11/00
See application file for complete search history.

(56) References Cited

U.S. PATENT DOCUMENTS

| | | | |
|---|---|---|---|
| 2,517,772 A | 8/1950 | Doub | |
| 3,364,200 A | 11/1961 | Ashton et al. | |
| 4,442,655 A * | 4/1984 | Stroetmann | A61K 38/363 106/124.1 |
| 4,626,253 A | 12/1986 | Broadnax, Jr. | |
| 5,100,509 A | 3/1992 | Pisecky | |
| 5,134,229 A | 7/1992 | Saferstein et al. | |
| 5,180,398 A | 1/1993 | Boardman et al. | |
| 5,484,913 A | 1/1996 | Stilwell et al. | |
| 5,645,849 A | 7/1997 | Pruss et al. | |
| 5,696,191 A | 12/1997 | Nohr et al. | |
| 6,113,948 A | 9/2000 | Heath et al. | |
| 6,162,241 A | 12/2000 | Coury et al. | |
| 6,177,126 B1 | 1/2001 | Hagedorn et al. | |
| 6,200,587 B1 | 3/2001 | Soe et al. | |
| 6,225,461 B1 | 5/2001 | Akimoto et al. | |
| 6,309,454 B1 | 10/2001 | Harvey et al. | |
| 6,596,318 B2 | 7/2003 | Prasch et al. | |
| 6,627,749 B1 | 9/2003 | Kumar | |
| 6,733,774 B2 | 5/2004 | Stimmeder | |
| 6,762,336 B1 | 7/2004 | MacPhee et al. | |
| 7,052,713 B2 | 5/2006 | Stimmeder | |

(Continued)

FOREIGN PATENT DOCUMENTS

| | | |
|---|---|---|
| CN | 101716383 | 6/2010 |
| CN | 102091347 A | 6/2011 |

(Continued)

OTHER PUBLICATIONS

DeAnglis, Ashley P et al. "A method to measure thrombin activity in a mixture of fibrinogen and thrombin powders." Blood coagulation & fibrinolysis : an international journal in haemostasis and thrombosis vol. 28,2 (2017) (Year: 2016).*

De Vries, Auke et al. "Controlling Agglomeration of Protein Aggregates for Structure Formation in Liquid Oil: A Sticky Business." ACS applied materials & interfaces vol. 9,11 (2017): 10136-10147. doi:10.1021/acsami.7b00443 (Year: 2017).*

(Continued)

*Primary Examiner* — Louise W Humphrey
*Assistant Examiner* — Anjali Ajit Hirani
(74) *Attorney, Agent, or Firm* — David R. Crichton; Leo B. Kriksunov

(57) ABSTRACT

The present invention is directed to hemostatic compositions comprising at least partially integrated agglomerated ORC fibers, fibrinogen, and thrombin and methods of forming a powdered hemostatic composition, comprising the steps of: forming a suspension of a mixture comprising particles of fibrinogen, thrombin, ORC fibers in a non-aqueous low boiling solvent, agitating and shearing said suspension in a high shear mixing reactor, adding water to allow particles to agglomerate, allowing the non-aqueous solvent to evaporate, drying and sieving the composition; and thus forming the powdered hemostatic composition.

5 Claims, 19 Drawing Sheets

(56) References Cited

U.S. PATENT DOCUMENTS

| | | | |
|---|---|---|---|
| 7,094,428 | B2 | 8/2006 | Spillert et al. |
| 7,189,410 | B1 | 3/2007 | Drohan et al. |
| 7,351,422 | B2 | 4/2008 | Jo et al. |
| 7,473,543 | B2 | 1/2009 | Jiang et al. |
| 7,666,803 | B2 | 2/2010 | Shetty et al. |
| 8,815,832 | B2* | 8/2014 | Wang .................. A61L 26/009 514/57 |
| 8,840,877 | B2 | 9/2014 | Adamson et al. |
| 8,846,105 | B2 | 9/2014 | Koopman et al. |
| 9,358,318 | B2* | 6/2016 | Gorman .................. A61K 9/70 |
| 9,717,821 | B2 | 8/2017 | Schutte et al. |
| 9,724,213 | B2 | 8/2017 | Zhang et al. |
| 9,795,773 | B2 | 10/2017 | Boyes et al. |
| 10,053,519 | B2 | 8/2018 | Goerlach-doht et al. |
| 2004/0005350 | A1 | 1/2004 | Looney et al. |
| 2004/0265371 | A1 | 12/2004 | Looney |
| 2006/0088589 | A1 | 4/2006 | Gorman et al. |
| 2006/0159733 | A1 | 7/2006 | Pendharkar et al. |
| 2006/0233869 | A1 | 10/2006 | Looney et al. |
| 2006/0257458 | A1 | 11/2006 | Gorman et al. |
| 2008/0027365 | A1 | 1/2008 | Huey |
| 2010/0119563 | A1 | 5/2010 | Smiyagawa et al. |
| 2013/0316974 | A1 | 11/2013 | Wang et al. |
| 2013/0323315 | A1 | 12/2013 | Blaskovich |
| 2014/0220103 | A1* | 8/2014 | Bacchetta ......... A61F 13/00012 424/445 |
| 2014/0036999 | A1 | 12/2014 | Schutte et al. |
| 2014/0369991 | A1 | 12/2014 | Schutte et al. |
| 2015/0017225 | A1 | 1/2015 | Hubbell |
| 2016/0015792 | A1* | 1/2016 | Hendricus van Pinxteren ............ A61K 9/16 424/94.64 |
| 2016/0074602 | A1 | 3/2016 | Wang |
| 2016/0193381 | A1 | 7/2016 | Olson |
| 2017/0128618 | A1 | 5/2017 | Wang |
| 2018/0043054 | A1 | 2/2018 | Chen et al. |
| 2018/0311405 | A1 | 11/2018 | Wang |

FOREIGN PATENT DOCUMENTS

| | | |
|---|---|---|
| CN | 102892393 A | 1/2013 |
| CN | 102892439 A | 1/2013 |
| CN | 104321085 A | 1/2015 |
| CN | 104721878 | 4/2015 |
| CN | 104812827 A | 7/2015 |
| CN | 105188740 A | 12/2015 |
| CN | 105536039 A | 5/2016 |
| CN | 105617453 A | 6/2016 |
| CN | 103957947 B | 9/2018 |
| DE | 19859611 C2 | 7/2003 |
| EP | 1323436 | 7/2003 |
| EP | 918548 | 8/2003 |
| EP | 1493451 | 9/2010 |
| EP | 1809343 | 8/2012 |
| JP | 2005015484 A | 1/2005 |
| JP | 2015-503368 A | 2/2015 |
| JP | 2015517388 A | 6/2015 |
| KR | 804434 | 2/2008 |
| KR | 2014/0086072 A | 7/2014 |
| KR | 20140086072 A | 7/2014 |
| KR | 1588633 | 1/2016 |
| KR | 1624625 | 5/2016 |
| RU | 2235539 | 9/2004 |
| RU | 2522980 C1 | 7/2014 |
| WO | WO 2001/024841 | 4/2001 |
| WO | WO 2004/064878 | 8/2004 |
| WO | WO 2007/076415 | 7/2007 |
| WO | 2010/071584 A1 | 6/2010 |
| WO | WO 2014/135689 | 9/2014 |
| WO | 2016064487 A2 | 4/2016 |

OTHER PUBLICATIONS

Cullen, B. et al "The role of oxidized regenerated cellulose/collagen in chronic wound repair and its potential mechanism of action" The International Journal of Biochemistry & Cell Biology (2002) 34 pp. 1544-1556.

Howsmon, J.A. et al "The Ball-Milling of Cellulose Fibers and Recrystallization Effects" Journal of Applied Polymer Science (1959) vol. 1, Issue 3, pp. 313-322.

Rajkhowa, R. et al. Ultra-fine silk powders powder preparation through rotary and ball milling Powder Technology (2008)185 pp. 87-95.

Yasnitskii, B.G. et al., 'Oxycelodex, a new hemostatic preparation' Pharmaceutical Chemistry Journal (1983) vol. 18, No. 4, pp. 506-508 (Abstract 2 pages).

International Search Report re: PCT/IB2017/054884 dated Dec. 1, 2017.

International Search Report re: PCT/US2016/059429 dated Feb. 28, 2017.

Written Opinion re: PCT/US2016/059429 dated Feb. 28, 2017.

U.S. Appl. No. 62/251,773.

U.S. Appl. No. 16/031,111, filed Jul. 10, 2018, 2018/0311405, Pending, Wang.

U.S. Appl. No. 15/337,337, filed Oct. 28, 2016, 2017/0128618, U.S. Pat. No. 10,034,957, Jul. 31, 2018, Granted, Wang.

U.S. Appl. No. 62/251,773, filed Nov. 6, 2015, Expired, Wang.

U.S. Appl. No. 62/371,954, Aug. 8, 2016, Expired, Wang.

U.S. Appl. No. 62/408,176, filed Oc. 14, 2016, Expired, Wang.

U.S. Appl. No. 15/258,549, filed Sep. 7, 2016, 2018/0043054, Pending, Chen et al.

Nichols et al., "A review of the terms agglomerate and aggregate with a recommendation for nomenclature used in powder and particle characterization", Journal of Pharmaceutical Sciences (2002) 91(1):2103-2109.

Wikipedia "Surgicel", last edited Nov. 1, 2017, https://en.wikipedia.org/wiki/Surgicel.

Written Opinion re: PCT/IB2017/054884 dated Dec. 1, 2017.

?, Thomson Scientific London GB, Thomson Scientific London GB, Jun. 24, 2015, pp. 1-4, page number.

?, Thomson Scientific London GB, Thomson Scientific London GB, Sep. 10, 2004, pp. 1-1, page Number.

De Vries, et al., Controlling Agglomeration of Protein Aggregates for Structure Formation in Liquid Oil:A Sticky Business, ACS Applied Materials & INTERFACES, Feb. 22, 2017, p. 10136-10147, vol. 9 Issue 11.

Deanglis, et al., A method to measure thrombin activity in a mixture of fibrinogen and thrombin powders, Blood Coagulation and Fibrinolysis, 2017, pp. 134-138, vol. 28 Issue 2.

Filatov et,al., Method for preparing powder-like material for cessation bleeding, Clarivate Analytics, Sep. 10, 2004, pp. 1-1, vol. 2007 Issue 70.

Fu Y et, al., Preparing hemostatic material useful for eg ; stopping bleeding in trauma surgery by preparing absorbent surface by electrostatic spinning fibrinogen and thrombin solution and drying absorbent., Clarivate Analytics, Jun. 24, 2015, pp. 1-4, vol. 2016 Issue 12.

Lewis, et al., Comparison of regenerated and non-regenerated oxidized cellulose hemostatic agents, European Surgery, 2013, pp. 213-220, vol. 45.

\* cited by examiner

FIG. 9
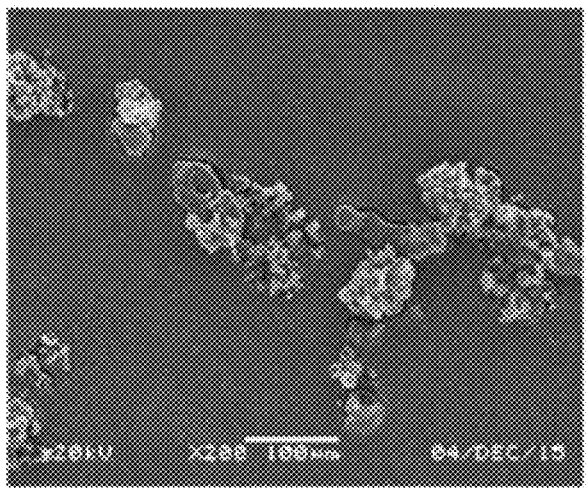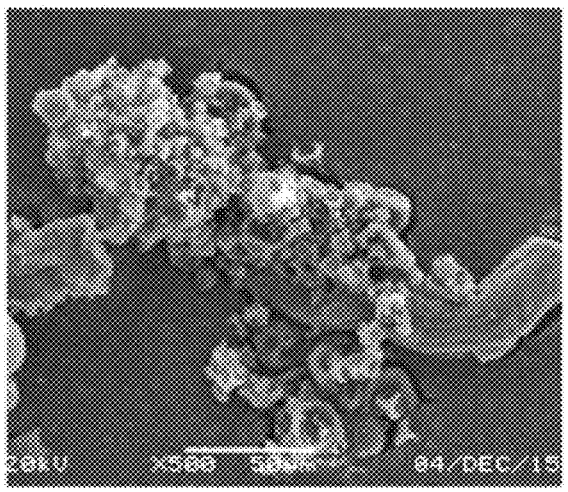

FIG. 10

Preparing dry powder mixtures of fibrinogen, thrombin, ORC, optionally calcium chloride, and optionally buffer compounds such as Tris and/or lysine

↓

Suspending dry powders mixture in a non-aqueous solvent capable of rapid evaporation under ambient conditions in a High Shear Mixer reactor

↓

Agitating the suspension with high speed shear blade and optionally continuously mixing the components simultaneously

↓

Introducing a small amount of water into the reactor to aid particles binding/aggregation/clumping

↓

Allowing the non-aqueous solvent to evaporate from the reactor; drying the resulting hemostatic material

↓

Removing the resulting hemostatic material from the HSM reactor and optionally sieving, thus forming at least partially integrated ORC fibers, fibrinogen, and thrombin in a form of an aggregated powder FIG. 14
| Image of animal study | Test result |
|---|---|
| acetone / RG502 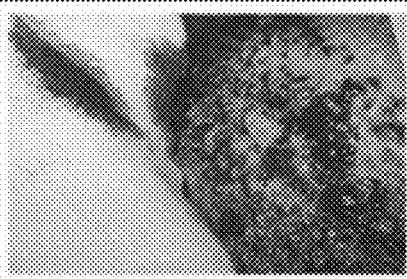 | After 3 minutes, oozing |
| acetone/water  | After 3 minutes, oozing |
| ethanol/water 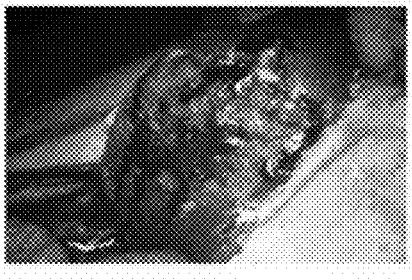 | After 3 minutes, oozing |
| HFE/water  | Stop bleeding within 1 minute |

HEMOSTATIC COMPOSITIONS AND METHODS OF MAKING THEREOF

FIELD OF THE INVENTION

The present invention relates generally to agents and materials for promoting hemostasis and tissue sealing and, more particularly, to resorbable hemostatic particulates with improved efficacy, particularly particulate aggregates made of fibrinogen, thrombin, and oxidized regenerated cellulose, and to methods for manufacturing such compositions.

BACKGROUND

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites. The control of bleeding is essential and critical in surgical procedures to minimize blood loss, to reduce post-surgical complications, and to shorten the duration of the surgery in the operating room. The selection of appropriate methods or products for the control of bleeding is dependent upon many factors, which include but are not limited to bleeding severity, anatomical location of the source and the proximity of adjacent critical structures, whether the bleeding is from a discrete source or from a broader surface area, visibility and precise identification of the source and access to the source.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized.

To address the above-described problems, materials have been developed for controlling excessive bleeding or as adjuncts to hemostasis. Topical Absorbable Hemostats (TAHs) are widely used in surgical applications. TAHs encompass products in various forms, such as based on woven or non-woven fabrics or sponges, and are typically made of at least partially resorbable materials, ranging from natural to synthetic polymers and combinations thereof, including lactide-glycolide based co-polymers such as polyglactin 910, oxidized cellulose, oxidized regenerated cellulose (ORC), gelatin, collagen, chitin, chitosan, starch etc. Gelatin is used in various forms with or without a topical thrombin solution. Also, widely used are biologically active topical hemostatic products (topical thrombin solutions, fibrin sealants, etc.) and a variety of synthetic topical sealants.

To improve the hemostatic performance, scaffolds based on the above mentioned TAH materials can be combined with biologically-derived clotting factors, such as thrombin and fibrinogen.

Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. Many methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber.

The ORC was introduced in 1960s offering safe and effective hemostasis for many surgical procedures. The mechanism of action for ORC hemostats is believed to start with the material absorbing water and then swelling slightly to provide tamponade at the bleeding site. The ORC fibers initially entrap fluid, blood proteins, platelets and cells forming a gel-like "pseudo-clot" which acts as a barrier to blood flow, and subsequently as a matrix for solid fibrin clot formation. The ORC fabric has a loose knit in its matrix structure and conforms rapidly to its immediate surroundings and easier to manage than other absorbable agents because it does not stick to surgical instruments and its size can be easily trimmed. This allows the surgeon to hold the cellulose firmly in place until all bleeding stops.

One of the most commonly used topical hemostatic agents is SURGICEL® Original Absorbable Hemostat, made of an Oxidized Regenerated Cellulose (ORC). SURGICEL® Absorbable Hemostat is used adjunctively in surgical procedures to assist in the control of capillary, venous, and small arterial hemorrhage when ligation or other conventional methods of control are impractical or ineffective. The SURGICEL® Family of Absorbable Hemostats consists of four main product groups, with all hemostatic wound dressings commercially available from Johnson & Johnson Wound Management Worldwide, a division of Ethicon, Inc., Somerville, N.J., a Johnson & Johnson Company:

SURGICEL® Original Hemostat is a white fabric is with a pale-yellow cast and has a faint, caramel like aroma. It is strong and can be sutured or cut without fraying.

SURGICEL® NU-KNIT® Absorbable Hemostat is similar but has a denser knit and thus a higher tensile strength. It is particularly recommended for use in trauma and transplant surgery as it can be wrapped or sutured in place to control bleeding.

The SURGICEL® FIBRILLAR™ Absorbable Hemostat form of the product has a layered structure which allows the surgeon to peel off and grasp with forceps any amount of SURGICEL® FIBRILLAR™ Hemostat needed to achieve hemostasis at a particular bleeding site. The SURGICEL® FIBRILLAR™ Hemostat form may be more convenient than the knitted form for hard to reach or irregularly shaped bleeding sites. It is particularly recommended for use in orthopedic/spine and neurological surgery.

The SURGICEL® SNoW™ Absorbable Hemostat form of the product is a Structured Non-Woven fabric. SURGICEL® SNoW™ Hemostat may be more convenient than other forms of SURGICEL® for endoscopic use due to the Structured Non-Woven fabric. It is highly adaptable and recommended in both open and minimally invasive procedures.

Other examples of commercial resorbable hemostats containing oxidized cellulose include GelitaCel® resorbable cellulose surgical dressing from Gelita Medical BV, Amsterdam, The Netherlands. The commercially available oxidized cellulose hemostats noted above are knitted or nonwoven fabrics having a porous structure for providing hemostasis.

Fibrinogen and thrombin are critical proteins involved in achieving hemostasis after vascular injury and essential to blood clot formation. Fibrinogen and thrombin can be combined in powder form or in a non-aqueous suspension, without initiating a typical clotting reaction, thus preventing the formation of a fibrin clot until the proteins are hydrated in an aqueous medium or other liquid environment in which the proteins are soluble. An admixture of these proteins in powder form have a variety of potential biomedical applications including topical hemostasis, tissue repair, drug delivery, etc. In addition, an admixture of these proteins may be loaded onto a carrier or substrate, or other medical device, in powder form to form a product that may be used for example as a hemostatic device.

Fibrin sealants, also known as fibrin glue, have been in use in the clinic for decades. Oftentimes, fibrin sealant consists of two liquid components, a fibrinogen comprising component and a thrombin comprising component, which are stored frozen due to their inherent instability. Sometimes fibrin sealant products consist of two freeze dried components, which require reconstitution immediately prior to use and delivery by a conjoined syringe or other double-barreled delivery device. Freeze dried formulations are typically stable, but the fibrinogen component is difficult to reconstitute. Many hemostatic formulations currently available on the market or in development utilize lyophilized fibrinogen, frequently in combination with lyophilized thrombin, with hemostatic formulations applied in the form of dry powder, semi-liquid paste, liquid formulation, or optionally disposed on a supporting scaffold such as absorbable fabric scaffold.

To provide dressings with enhanced hemostatic and tissue sealing and adhering properties, therapeutic agents, including, but not limited to, thrombin, fibrin and fibrinogen have been combined with dressing carriers or substrates, including gelatin-based carriers, polysaccharide-based carriers, glycolic acid or lactic acid-based carriers and a collagen matrix. Examples of such dressings are disclosed in U.S. Pat. No. 6,762,336 Hemostatic sandwich bandage, U.S. Pat. No. 6,733,774 Carrier with solid fibrinogen and solid thrombin, PCT publication WO2004/064878 Hemostatic Materials, and European Patent EP1809343B1 A reinforced absorbable multilayered hemostatic wound dressing and method of making.

European Patent No. EP1493451B1 "Haemostatic devices and compositions comprising oxidized cellulose particles and a polysaccharide binder" discloses that it is problematic to use the carboxylic-oxidized cellulose as a carrier for acid-sensitive species, such as thrombin and fibrinogen, as well as other acid-sensitive biologics and pharmaceutical agents. It further discloses a haemostatic composition, consisting of: biocompatible, oxidized cellulose particles having an average designated nominal particle size of from 0.035 to 4.35 mm; a biocompatible, porous, water-soluble polysaccharide binder component other than chitosan; and optionally, a haemostatic agent selected from thrombin, fibrinogen or fibrin, wherein the weight ratio of said water-soluble polysaccharide to said oxidized cellulose particles is from 3:97 to 15:85, and wherein said composition is a porous foam sponge obtainable by a process comprising the steps of: providing a polymer solution having said polysaccharide binder component dissolved in a suitable solvent, providing said biocompatible, oxidized cellulose particles, contacting said polymer solution with said oxidized cellulose particles under conditions effective to disperse said oxidized cellulose particles substantially homogenously throughout said polymer solution to form a substantially homogenous dispersion, subjecting said polymer solution having said particles dispersed throughout to conditions effective to solidify said substantially homogenous dispersion; and removing said solvent from the solidified dispersion, thereby forming said haemostatic composition.

Russian patent publication RU2235539C1 "Method for preparing powder-like material for cessation bleeding" discloses method for preparing powder-like material eliciting hemostatic effect involves mixing partially oxidized cellulose as a base in an aqueous medium with thrombin and fibrinogen. Gelatin, epsilon-aminocaproic acid and lysozyme are added to indicated substances additionally, and dialdehyde cellulose as fabric is used as partially oxidized cellulose, i.e the content of aldehyde groups is from 4 to 6% in the following ratio of components: dialdehyde cellulose, 1 g; fibrinogen, 18-22 mg; gelatin, 27-33 mg; epsilon-aminocaproic acid, 45-55 mg; lysozyme, 9.5-10.5 mg; thrombin, 350 U; water, 6.5 ml. Method involves preparing solution containing fibrinogen, epsilon-aminocaproic acid in one-half amount of total content of gelatin and one-half amount of total content of water, and separated preparing solution of thrombin, lysozyme and remained amount of gelatin in remained amount of water. In prepared solutions, one-half amount of dialdehyde cellulose is kept for 3-4 h, semi-finished products are squeezed, dried in air and subjected for the combined grinding.

U.S. patent publication No. 20060159733A1 "Method of providing hemostasis to a wound" discloses that the acidic nature of carboxylic oxidized cellulose substrate could rapidly denature and inactivate acid sensitive proteins, including thrombin or fibrinogen, on contact. Much of the enzymatic activity of thrombin and Factor XIII could be lost during the reaction. This makes it difficult to use the carboxylic-oxidized cellulose as a carrier for thrombin, fibrinogen, fibrin, or other acid sensitive biologics and pharmaceutical agents. It further discloses that hemostatic wound dressings containing neutralized carboxylic-oxidized cellulose and protein based-hemostatic agents, such as thrombin, fibrinogen and fibrin are known. Neutralized carboxylic-oxidized cellulosic materials are prepared by treating the acidic carboxylic-oxidized cellulose with a water or alcohol solution of a basic salt of a weak organic acid to elevate the pH of the cellulosic material to between 5 and 8 by neutralizing the acid groups on the cellulose prior to addition of thrombin to make it thrombin compatible. A thrombin hemostatic patch was disclosed, wherein thrombin was added to an acidic carboxylic oxidized regenerated cellulose or other material in presence of an acid neutralizing agent, epsilon aminocaproic acid (EACA), to raise the pH of the material to a region where thrombin can perform as a hemostat. While such neutralized carboxylic-oxidized cellulose may be thrombin compatible, it is no longer bactericidal, because the anti-microbial activity of oxidized cellulose is due to its acidic nature.

U.S. Pat. No. 7,094,428B2 "Hemostatic compositions, devices and methods" discloses a hemostatic composition which comprises at least one procoagulant metal ion, such as silver (I) or mercury (II), and at least one procoagulant biopolymer, such as collagen, thrombin, prothrombin, fibrin, fibrinogen, heparinase, Factor VIIa, Factor VIII, Factor IXa, Factor Xa, Factor XII, von Willebrand Factor, a selectin, a procoagulant venom, a plasminogen activator inhibitor, glycoprotein IIb-IIIc, a protease, or plasma. The composition in the form of a paste, dough, glue, liquid, lyophilized powder or foam, may be provided, for application to a wound. A hemostatic composition comprising at least one procoagulant biopolymer in combination with a procoagulant metal ion, said procoagulant metal ion present in said composition at a level below its effective hemostatic concentration in the absence of said procoagulant biopolymer wherein the hemostatic composition is selected from the group consisting of silver (I) and collagen, silver (I) and thrombin, silver (I) and prothrombin, silver (I) and fibrin, silver (I) and fibrinogen, silver (I) and heparinase, silver (I) and Factor VIIa, silver (I) and Factor VIII, silver (I) and Factor IXa, silver (I) and Factor Xa, silver (I) and Factor XII, silver (I) and von Willebrand Factor, silver (I) and a selectin, silver (I) and a procoagulant venom, silver (I) and a plasminogen activator inhibitor, silver (I) and glycoprotein IIb-IIIa, silver (I) and a protease, silver (I) and plasma, mercury (II) and collagen, mercury (II) and thrombin, mercury (II) and prothrombin, mercury (II) and fibrin, mercury (II) and fibrinogen, mercury (II) and heparinase, mercury (II) and Factor VIIa, mercury (II) and Factor VIII, mercury (II) and Factor IXa, mercury (II) and Factor Xa, mercury (II) and Factor XII, mercury (II) and von Willebrand Factor, mercury (II) and a selectin, mercury (II) and a procoagulant venom, mercury (II) and a plasminogen activator inhibitor, mercury (II) and glycoprotein IIb-IIIa, mercury (II) and a protease, and mercury (II) and plasma. The hemostatic composition of the invention may also include a carrier, such as, but not limited to, polyethylene glycol, hyaluronic acid, cellulose, oxidized cellulose, methyl cellulose, or albumin. These may be used to provide a matrix, a suitable viscosity, deliverability, adherence, or other properties desired to be imparted to the compositions herein for easy in application to a wound. Numerous other carrier which impart these characteristics are embraced herein.

U.S. Pat. No. 6,162,241A "Hemostatic tissue sealants" discloses a hemostatic tissue sealant, comprising: a biocompatible, biodegradable hydrogel tissue sealant comprising crosslinkable groups having incorporated therein an effective amount of a hemostatic agent to stop the flow of blood from tissue in a medically acceptable period of time.

U.S. Pat. No. 6,177,126B1 "Process for the production of a material for sealing and healing wounds" discloses a process for the production of a material for sealing and/or healing wounds, comprising: i) filling a liquid composition into a container having two or more plates, at least two of said plates being perforated with one or more flow-through holes and at least one of said perforated plates being movable relative to another of said perforated plates, ii) transporting a carrier below the container in a transport direction, and iii) continuously moving the perforated plates relative to each other so as to allow the liquid composition to drip on to the carrier being transported below the container, whereby the liquid composition is substantially evenly applied to the carrier.

PCT publication No. WO2014135689A2 "Powder formulation" discloses a sterile powder composition suitable for medical use comprising thrombin and fibrinogen, wherein the thrombin powder is produced from a liquid feedstock, wherein the feedstock comprises a solution or a suspension of thrombin, preferably a solution, wherein the powder is produced by removal of liquid by a process selected from aseptic spray drying or aseptic fluid bed drying, and wherein the powder resulting from removal of liquid from the feedstock exhibits at least 80% of the thrombin potency or activity of the liquid feedstock, and wherein the fibrinogen powder is produced by removal of liquid from a feedstock, wherein the feedstock comprises a solution or a suspension of fibrinogen, preferably a solution, by aseptic spray drying or aseptic fluid bed drying, and wherein said composition is packaged as a sterile final pharmaceutical product for medical use.

U.S. Patent Publication No: 2010/0119563 "SOLID FIBRINOGEN PREPARATION" discloses a solid fibrinogen preparation comprising fibrinogen and further comprising: (a) albumin; (b) a nonionic surfactant; (c) a basic amino acid or a salt thereof; and (d) at least two amino acids or a salt thereof selected from the group consisting of an acidic amino acid, a salt thereof, a neutral amino acid and a salt thereof.

Additional patent documents related to formulating hemostatic formulations include:

U.S. Pat. No. 9,717,821B2 Formulations for wound therapy

U.S. Pat. No. 7,052,713B2 Carrier with solid fibrinogen and solid thrombin

U.S. Pat. No. 9,724,213B2 Nanocrystalline cellulose materials and methods for their preparation U.S. Pat. No. 8,840,877B2 Polysaccharide-protein conjugates reversibly coupled via imine bonds U.S. Pat. No. 6,200,587B1 Tissue sealant containing fibrinogen, thrombin and carboxymethyl cellulose or salt thereof U.S. Pat. No. 8,846,105B2 Dry powder fibrin sealant

US20160015792A1 POWDER FORMULATION COMPRISING THROMBIN AND FIBRINOGEN

U.S. Pat. No. 6,596,318B2 Fibrin tissue adhesive formulation and process for its preparation KR1624625B1 Improved absorbable hemostatic material and method for preparing the same KR1588633B1 Composition and kit for forming gel for hemostasis and adhesion inhibition|

KR804434B1 Fibrin-based glue granulate and corresponding production method|Fibrin-based glue granulate and a method of manufacturing the same.

U.S. Pat. No. 9,795,773B2 Medicament unit dose cartridge and delivery device

U.S. Pat. No. 7,351,422B2 Hemostatic soluble cellulose fibers containing coagulating protein for treating wound and process for producing the same CN101716383A Preparation method of bleeding stopping and adherence preventing material|Preparation method for stanching and anti-blocking material U.S. Pat. No. 5,484,913A Calcium-modified oxidized cellulose hemostat EP918548B1 USE OF OXIDIZED CELLULOSE AND COMPLEXES THEREOF FOR CHRONIC WOUND HEALING There is a need in improved hemostatic forms and materials which facilitate ease of application and rapid onset of hemostasis.

SUMMARY OF THE INVENTION

The present invention is directed to a hemostatic material comprising aggregates comprising fibrinogen, thrombin, and oxidized regenerated cellulosic fibers. In some aspects, the hemostatic material further includes additives, such as calcium chloride, Tris. In another aspect, the present invention is directed to a method of making the hemostatic materials described above by suspending a mixture of fibrinogen, thrombin, and ORC powders in a non-aqueous solvent, spraying the suspension through a nozzle onto a substrate, removing the hemostatic material from the substrate and sieving.

In yet another aspect, the present invention is directed to a method of treating a wound by applying the hemostatic materials described above onto and/or into the wound of a patient.

In one embodiment, the present invention relates to methods of forming a powdered hemostatic composition by forming a suspension of a mixture comprising particles of fibrinogen, thrombin, ORC fibers in a non-aqueous low boiling solvent; spraying the suspension through a nozzle onto a substrate, allowing the non-aqueous solvent to evaporate; separating the composition from the substrate and sieving the composition; and thus, forming the powdered hemostatic composition. The non-aqueous low boiling solvent can be hydrofluoroether $C_4F_9OCH_3$, such as but not limited to HFE7100. The suspension can further include Tris and/or calcium chloride. The liquid suspension can contain a fibrin sealant powder which comprises about 90% of fibrinogen, about 8% of thrombin, and about 2.5% calcium chloride by weight. The suspended powdered hemostatic composition can have a ratio of fibrin sealant powder to ORC from about 1:1 to about 10:1 by weight. The suspended powdered hemostatic composition can be in the form of a powder having a measured particle size predominantly in the range from about 250 to about 850 microns, more preferably from about 355 to about 850 microns. The resulting powdered hemostatic composition comprises at least partially integrated agglomerated ORC fibers, fibrinogen, and thrombin and can further comprise Tris and/or calcium chloride.

The present invention is further directed to methods of treating a wound by applying the resulting hemostatic composition described above onto and/or into the wound.

BRIEF DESCRIPTION OF FIGURES

FIG. 9 is showing SEM images of one of inventive compositions.

FIG. 10 is a schematic diagram of the HSM manufacturing process.

FIG. 14 shows the results of testing in animal model of the hemostatic powders made by using different solvents/binders.

DETAILED DESCRIPTION

The inventors have discovered hemostatic materials and process for making thereof, the hemostatic materials having surprising and highly beneficial properties for hemostasis.

The hemostatic material according to the present invention is made from oxidized cellulose-based fiber materials, more preferably form oxidized regenerated cellulose powder, fibrinogen powder, and thrombin powder. The hemostatic material according to the present invention represents at least partially integrated ORC fibers, fibrinogen, and thrombin in a form of a powder.

Figure 1:
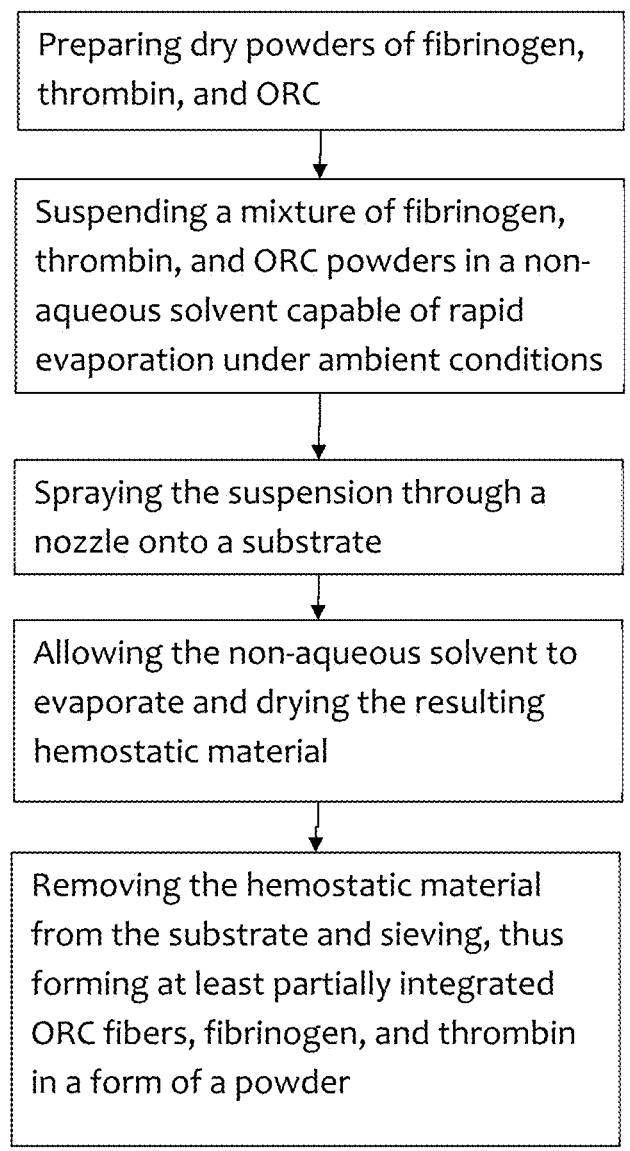
FIG. 1 is a schematic diagram of the manufacturing process.

Referring to FIG. 1, a schematic block-diagram of the process of making the hemostatic material according to the present invention is shown and comprises the steps of:

Preparing dry powders of fibrinogen, thrombin, and ORC

Suspending a mixture of fibrinogen, thrombin, and ORC powders in a non-aqueous solvent capable of rapid evaporation under ambient conditions Spraying the suspension through a nozzle onto a substrate Allowing the non-aqueous solvent to evaporate and drying the resulting hemostatic material Removing/separating the hemostatic material from the substrate and sieving, thus forming at least partially integrated ORC fibers, fibrinogen, and thrombin in a form of a powder In one embodiment, Tris, or Tris(hydroxymethyl)aminomethane buffer in a powder form is added to the fibrinogen, thrombin, and ORC mixture for pH adjustment. Then the mixed composition was added to HFE to form a suspension. In one embodiment, the cooling/chilling effect of the material stream during spraying due to HFE evaporation allows some ambient moisture to be absorbed onto or into the resulting hemostatic material. Any excessive moisture thus absorbed is removed in the final drying step in vacuum oven drying.

According to one aspect of the present invention, the ratio of fibrinogen/thrombin mixture to ORC powder in the inventive hemostatic material is from about 1:1 to about 10:1 by weight.

According to one aspect of the present invention the inventive hemostatic material comprises particles having size of 250-850 microns.

According to one aspect of the present invention the inventive hemostatic material comprises substantially uniformly distributed at least partially integrated ORC fibers, fibrinogen, and thrombin in a form of a powder According to one aspect of the present invention, the inventive hemostatic material has high uniformity, integration, fast gelling/clotting, and strong adhesion force.

According to one aspect of the present invention, the collecting surface or substrate onto which the suspension is sprayed, comprises an inert non-woven felt or mesh or a steel plate.

According to another embodiment of the present invention, the present invention is directed to a hemostatic material comprising aggregates comprising fibrinogen, thrombin, and oxidized regenerated cellulosic fibers. In some aspects, the hemostatic material further includes additives, such as calcium chloride, and a buffer, such as Tris and/or Lysine.

In another aspect, the present invention is directed to a method of making the hemostatic materials described above by suspending a mixture of fibrinogen, thrombin, and ORC powders in a non-aqueous solvent in a High Shear Mixing (HSM) apparatus, and performing high shear mixing and regular mixing and/or agitation, while allowing the volatile non-aqueous solvent to evaporate through any suitable port(s) such as through air seals of mixing blades/impellers and/or through a vacuum tube. Optionally, a small amount of water or aqueous solution is introduced into the reactor during mixing to aid particles binding/aggregation/clumping. The non-aqueous low boiling solvent can be hydrofluoroether $C_4F_9OCH_3$, such as but not limited to HFE7100.

According to an embodiment of the present invention, a hemostatic aggregated powder comprises ORC fine fibers or powder, thrombin, fibrinogen, lysine (as a buffer/pH adjusting agent), calcium salt.

According to an embodiment of the present invention, a process of making such powdered hemostatic product comprises the steps of mixing the individual components as powders with HFE, creating a suspension in HFE (volatile non-aqueous solvent) in High Shear mixing/shearing reactor, having a low speed mixing blade and high-speed shear blade. As mixing is performed, HFE can evaporate through air seals of mixing blades and/or vacuum tube. A small amount of water is introduced into the reactor to aid particles binding/aggregation/clumping.

According to an embodiment of the present invention, a method of making hemostatic powder, comprising the steps of: Forming a suspension of ORC powder, thrombin, fibrinogen, lysine, calcium salt in HFE (volatile non-aqueous solvent), agitating the suspension with high speed shear blade (and optionally continuously mixing the components simultaneously with a low speed mixer); Adding a small amount of water to the reactor to aid particles binding/aggregation/clumping; allowing HFE to evaporate from the reactor completely; Thus forming the hemostatic powder.

Example 1. Preparation of Hemostatic Compositions

The individual components of the hemostatic compositions of the present invention were prepared as described below.

Fibrinogen. Any method of preparation of fibrinogen powder can be utilized, including lyophilization, freeze drying, etc. In the instant example, fibrinogen powder was prepared by spray drying method (Spray dryer manufacturer: ProCepT, Model: 4M8-TriX). Fibrinogen solution is a formulation commercially available from Bioseal Biotech CO. LTD, located in Guangzhou, China, and comprising fibrinogen, albumin, and other needed reagents in WFI. The fibrinogen solution was first atomized through a spray nozzle in a hot airflow, then dried instantly. The spray drying parameters were as shown in Table 1

TABLE 1

| Feed Rate | 130 ml/h |
|---|---|
| Drying Columns | 3 (Mode II) |
| Column Air Flow | 0.6 m$^3$/min |
| Inlet Air Temperature | 150° C. |
| Nozzle Diameter | 0.8 mm |
| Atomizing Air Flow | 12 L/min |
| Cyclone Gas | 0.15 m$^3$/min |

Thrombin. Any method of preparation of thrombin powder can be utilized, including lyophilization, freeze drying, etc. In the instant example, thrombin powder was prepared by spray drying method with thrombin formulation solution. Thrombin solution was the formulation commercially available from Bioseal Biotech CO. LTD, located in Guangzhou, China, and comprising thrombin, albumin, and other needed reagents in WFI. The spray drying parameters were as shown in Table 2

TABLE 2

| Feed Rate | 258 ± 20 ml/h |
|---|---|
| Drying Columns | 2 |
| Column Air Flow | 0.3 m$^3$/min |
| Cooling Air Flow | 0.3 m$^3$/min |
| Inlet Air Temperature | 160° C. |
| Nozzle Diameter | 0.4 mm |
| Atomizing Air Flow | 7 L/min |
| Cyclone Gas | 0.1 m$^3$/min |

The thrombin and fibrinogen powders were then mixed together for preparation of the composite by the ratio of 89.7% of fibrinogen 7.8% of thrombin and 2.5% calcium chloride by weight, thus forming fibrin sealant powder.

The source of fibrinogen and thrombin was Porcine blood plasma which was fractionated to obtain fibrinogen and thrombin. and supplied by Bioseal Biotech CO. LTD, Located in Guangzhou, China The ORC powder can be obtained by processing of the Surgicel original fabric. A reference is made to the U.S. Provisional Patent Application No. 62/251,773 by Yi-Lan Wang, filed 6 Nov. 2015 and titled "Compacted Hemostatic Cellulosic Aggregates", which is incorporated by reference in its entirety for all purposes.

Briefly, the ORC powder was obtained by processing of the Surgicel original fabric in the following process:
1) split and cut the fabric into about 2"×8" pieces,
2) mill the fabrics into the powder particle size (D50 less than 94 microns) using known milling methods. One of the methods used in the preparations is the ball mill method— place ~100 grams of fabric into a 500-ml zirconia jar, then place 12 to 13 pieces of 20 mm zirconia balls (agates) into the same jar, cover and fix the jar in a Retsch planetary ball mill (Model PM100), mill the fabric with 450 rpm for 20 minutes, transfer the milled powders onto a 8" diameter and 300-micron opening sieve, separate the agates and the powders by slightly shaking, and collect the powders.

The inventive hemostatic compositions were prepared as follows by using co-spraying methods. 1 part of ORC fiber was combined with 1 part, or 2 parts, or 5 parts, or 10 parts of fibrin sealant powders, by weight. Thus, as an example, 10 g of ORC powder was combined with 10 g, 20 g, 50 g, or 100 g of fibrin sealant mixed powders, to produce 20 g, 30 g, 50 g, or 100 g of mixture.

A small amount of Tris was added to adjust pH to 7.0 for each respected ORC: Fibrin sealant ratio. pH was adjusted by placing the powder on a wetting surface and measuring the resulting pH and evaluating the amount of Tris needed for obtaining a neutral pH of 7. The sample was then discarded. A corresponding proportional amount of dry powder of Tris was then added to the powder mixture, prior to co-spraying.

ORC is not per se neutralized as Tris is added in dry form. ORC is being neutralized when the whole powder formulation is wetted during the application and the Tris is dissolved. A low boiling non-aqueous solvent was utilized for making a suspension of FS and ORC powders. Hydrofluoroether C4F9OCH3 was used, obtained as HFE 7100, for instance supplied by 3M as Novec 7100 Engineered Fluid, having boiling point of 61° C. HFE7100 solvent was added to the powders compositions and filtered through 150 µm sieve. The evenly distributed suspension was created by constantly agitating at 90 rpm/min in the reservoir at 20±5° C. temperature. The suspended components were sprayed through a 0.7 mm diameter nozzle. The type of the nozzle used was B1/8VAU-316SS+SUV67-316SS manufactured by Spraying Systems Co. The flow through the nozzle was at a flow rate of 130 ml/min, onto a non-woven fabric or stainless steel substrate at 20±5° C. temperature.

Upon spraying the suspension, most of the HFE 7100 solvent was evaporating. The HFE 7100 solvent residues and the absorbed ambient moisture in the powder, if any, could evaporate in a vacuum drying oven for 24 h±5 h at 20±5° C.

The resulting hemostatic composition was scooped off or peeled off or otherwise separated from the substrate, and sequentially passed through sieves having 850 µm, 355 µm, 250 µm openings.

Table 3 shows parameters used for co-spraying compositions

TABLE 3

PARAMETERS FOR CO-SPRAYING THE COMPOSITION

| | |
|---|---|
| -fan pressure | 0.3 bar |
| atomizing pressure | 3 bar |
| flow rate | 130 ml/min |
| liquid pressure | 16 kpa |
| Nozzle Diameter | 0.7 mm |
| agitation speed | 90 rpm/min |

As comparative examples, pure fibrin sealant mixture composition with no ORC and no Tris was also prepared by the same spray method HFE7100.

Example 2. Comparison of Mechanically Mixed Vs. Spray Mixed Hemostatic Compositions Gelling Rapid gelling and formation of strong gels is important for hemostatic materials.

The inventive hemostatic composition was prepared as described above by co-spray method.

The comparative mechanically mixed composition was prepared by manually shaking dry powders, i.e. FS and ORC powders obtained as described above, by manually shaking in a container into an evenly mixed composition, with no co-spraying performed. The compositions included all the same components, including Tris, with the difference being methods of mixing.

Fibrin sealant powder to ORC ratios tested were: Fibrin sealant (FS): ORC ratios—1:1; 2:1; 5:1; 10:1 (by weight). Thus for 1:1 FS/ORC ratio, 1 part of fibrin sealant powder (comprising fibrinogen, thrombin, calcium chloride) is combined with 1 part of ORC powder (by weight).

Mechanically mixed composition and the inventive spray mixed composition were then added to 20 ml of water in a 50-ml vial in the amount of 200 mg on the top of the water surface. After 2 min for gelling, the vial was turned upside down and observations made if a gelled layer of composition was formed in which case the water was observed sealed by the gelled layer and was held on the bottom of the vial by the formed gel layer.

Figure 2:
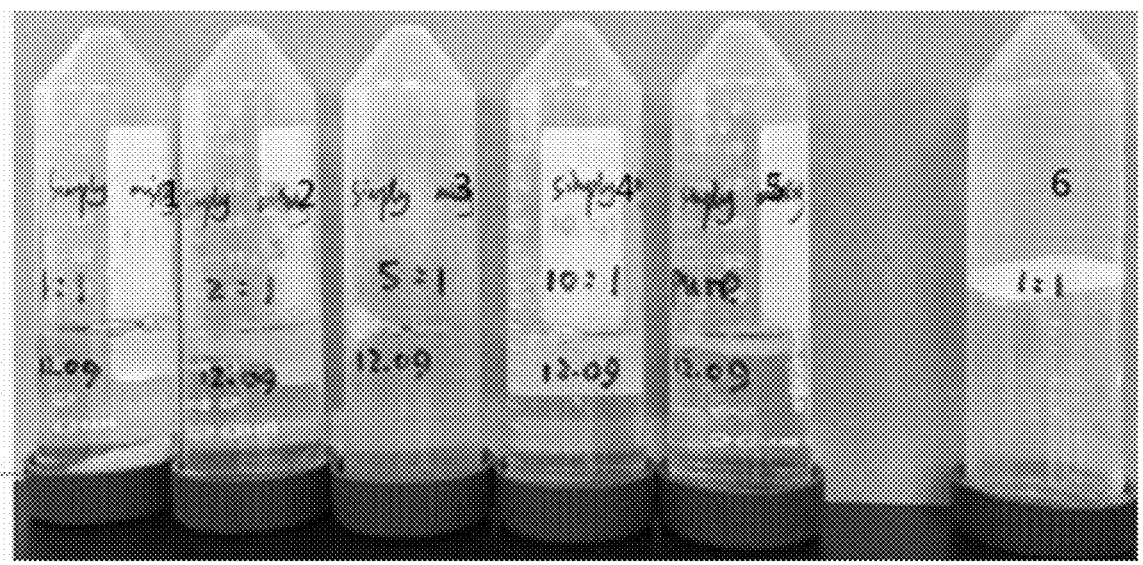
FIG. 2 is a photo showing test vials evaluating gelling of inventive and comparative compositions in water.

Referring now to FIG. 2, showing an image of the test vials turned upside down at the end of the test, with

- test vial 1 showing mechanically mixed composition 1:1 FS/ORC ratio
- test vial 2 showing mechanically mixed composition 2:1 FS/ORC ratio
- test vial 3 showing mechanically mixed composition 5:1 FS/ORC ratio
- test vial 4 showing mechanically mixed composition 10:1 FS/ORC ratio
- test vial 5 showing mechanically mixed composition with no ORC powder (fibrin sealant powder only)
- test vial 6 showing inventive hemostatic composition 1:1 FS/ORC ratio Analysis of the results shown in FIG. 2 indicates that in test vials 1-5 gelling was insufficient to hold the fluid and fluid is visible in the lower part of the vial. In test vial 6, fluid is visible in the upper part of the vial, i.e. water is being held by the gelled layer and prevented from moving to the lower part of the vial under gravitational force. Thus, for mechanically mixed compositions in all ratios and for fibrin sealant composition without ORC gelling was insufficient, while the inventive hemostatic composition prepared in 1:1 ratio exhibited surprisingly strong gelling.

Example 3. In Vitro Testing of Blood Clotting

In vitro clotting of blood by several inventive and comparative compositions was tested as follows.

20 ml of citrated whole blood (porcine) was added to a 50-ml vial. 200 mg of hemostatic compositions being tested were added on the top of the blood surface. After 2 min for clotting, the vial was turned upside down and observations of blood clotting were made. In case of complete clotting, the clotted blood stays in the upper part of the vial turned upside down. In case of incomplete clotting, blood remains fluid and drains towards the lower part of the vial due to the gravitational force.

Comparative excipients added to fibrin sealant powder instead of ORC were Trehalose, PEG4000, Mannitol, and Alfa-cellulose (α-cellulose). All excipients were purchased from Aladdin industrial corporation. Fibrin sealant powder mixtures with Trehalose, PEG 4000, Mannitol, or Alfa-cellulose were prepared by spray method as described above in 10:1 ratio, i.e. with 10 parts of fibrin sealant (FS) powder combined with 1 part of the respective excipient. The total amount of inventive and comparative compositions added to 20 ml of blood was 200 mg.

Figure 3:
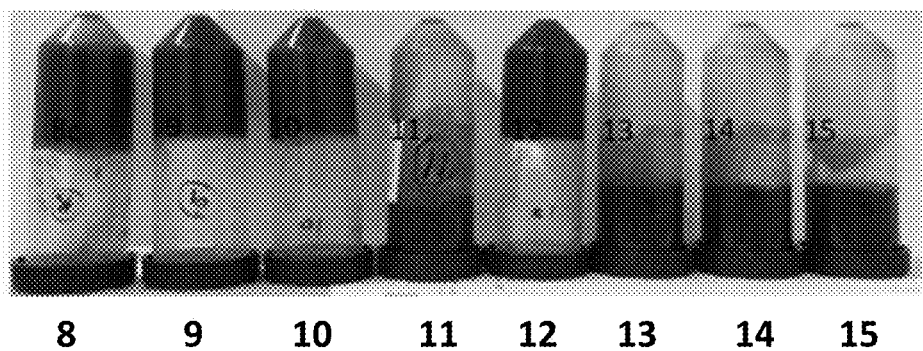
FIG. 3 is a photo showing test vials evaluating clotting of blood in contact with inventive and comparative compositions.

Referring now to FIG. 3, showing an image of the test vials turned upside down at the end of the test, with test vial 8 showing the inventive hemostatic composition having 2:1 FS/ORC ratio test vial 9 showing the inventive hemostatic composition having 5:1 FS/ORC ratio test vial 10 showing the inventive hemostatic composition having 1:1 FS/ORC ratio test vial 11 showing comparative composition comprising fibrin sealant powder only with no ORC made by co-spray test vial 12 showing comparative composition comprising fibrin sealant powder with addition of α-cellulose in 10:1 FS/α-cellulose ratio by weight test vial 13 showing comparative composition comprising fibrin sealant powder with addition of trehalose in 10:1 FS/trehalose ratio by weight test vial 14 showing comparative composition comprising fibrin sealant powder with addition of PEG4000 in 10:1 FS/PEG4000 ratio by weight test vial 15 showing comparative composition comprising fibrin sealant powder with addition of mannitol in 10:1 FS/mannitol ratio by weight Analysis of the results presented in FIG. 3 indicates that in test vials 8-10 containing the inventive hemostatic composition blood has clotted, with blood clot visible in the upper part of the vial turned upside down with clotted blood prevented from moving to the lower part of the vial under gravitational force. Thus, the inventive hemostatic composition prepared in 2:1; 5:1; 1:1 FS/ORC ratio exhibited surprisingly strong clotting of blood. Also, comparative sample containing α-cellulose in vial 12 shows clotting of blood. Comparative examples in vial 11 (fibrin sealant powder only with no ORC); vial 13 (fibrin sealant powder with addition of trehalose); vial 14 (fibrin sealant powder with addition of PEG4000); vial 15 (fibrin sealant powder with addition of mannitol) show no clotting or insufficient clotting, whereby clotting was insufficient to hold the fluid and fluid is visible in the lower part of the vial, i.e. blood remains fluid and drains towards the lower part of the vial due to the gravitational force. The inventive hemostatic compositions exhibited surprisingly strong blood clotting.

Figure 4:
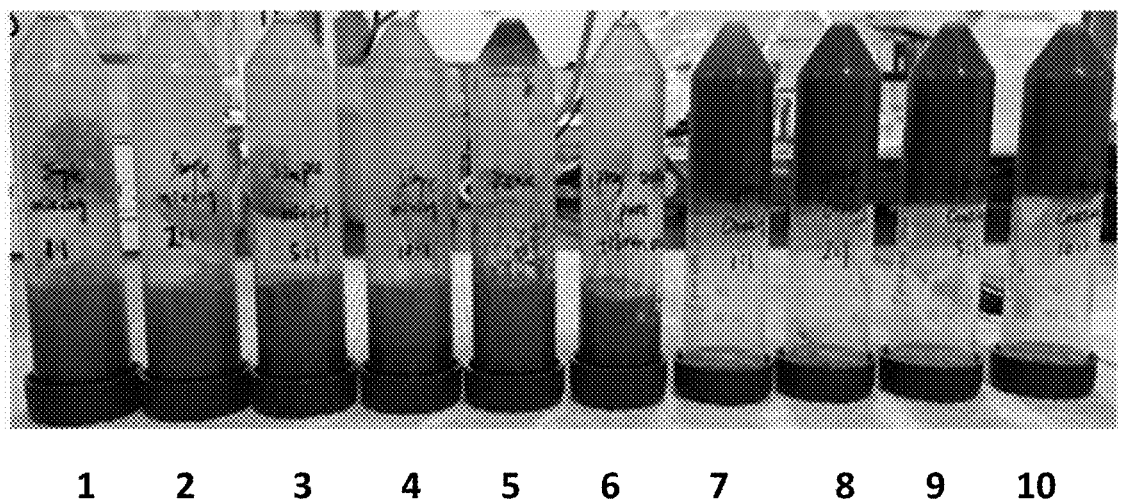
FIG. 4 is a photo showing test vials evaluating clotting of blood in contact with inventive and comparative compositions.

Using the same testing methods, additional in vitro blood clotting testing was performed for inventive hemostatic composition and comparative mechanically mixed compositions prepared by manually shaking dry powders in a container as well as for fibrin sealant powder only with no ORC Referring now to FIG. 4, showing an image of the test vials turned upside down at the end of the test, with test vial 1 showing mechanically mixed composition 1:1 FS/ORC ratio test vial 2 showing mechanically mixed composition 2:1 FS/ORC ratio test vial 3 showing mechanically mixed composition 5:1 FS/ORC ratio test vial 4 showing mechanically mixed composition 10:1 FS/ORC ratio test vial 5 showing comparative composition (200 mg) comprising compacted ORC powder aggregates prepared as described in the U.S. Provisional Patent Application No. 62/251,773 by Yi-Lan Wang, filed 6 Nov. 2015 and titled "Compacted Hemostatic Cellulosic Aggregates"

test vial 6 showing comparative composition comprising fibrin sealant powder only with no ORC prepared by co-spray method test vial 7 showing the inventive hemostatic composition having 1:1 FS/ORC ratio test vial 8 showing the inventive hemostatic composition having 2:1 FS/ORC ratio test vial 9 showing the inventive hemostatic composition having 5:1 FS/ORC ratio test vial 10 showing the inventive hemostatic composition having 10:1 FS/ORC ratio Analysis of the results presented in FIG. 4 indicates that comparative examples in test vials 1-6, containing mechanically mixed compositions in all ratios; ORC powder only; and fibrin sealant powder without ORC, show no clotting or insufficient clotting, whereby clotting was insufficient to hold the fluid and fluid is visible in the lower part of the vial, i.e. blood remains fluid and drains towards the lower part of the vial due to the gravitational force. On the contrary, and like the results presented in FIG. 3, in test vials 7-10, containing the inventive hemostatic composition, the blood has clotted, with blood clot visible in the upper part of the vial turned upside down with clotted blood prevented from moving to the lower part of the vial under gravitational force. Thus, the inventive hemostatic compositions prepared in 1:1-10:1 FS/ORC ratios exhibited surprisingly strong clotting of blood.

Example 4. Composition Solubilisation

Rapid solubilisation or solubility of a powdered hemostatic composition when in contact with bodily fluids can help to establish rapid hemostasis and indicates rapid interaction with fluids. The visual test of solubilisation was performed as follows: 1 gram of tested hemostatic powdered composition was evenly applied to an area of a wetting substrate which comprising a non-woven fabric positioned on top of a sponge material which was placed in a tray with pure water. After the tested powdered hemostatic composition was applied to the surface of the wetting substrate, visual observation of the composition solubility was performed and results recorded at zero time (immediately after applying the composition, at 1 min and at 2 min after applying the tested composition.

Figure 5:
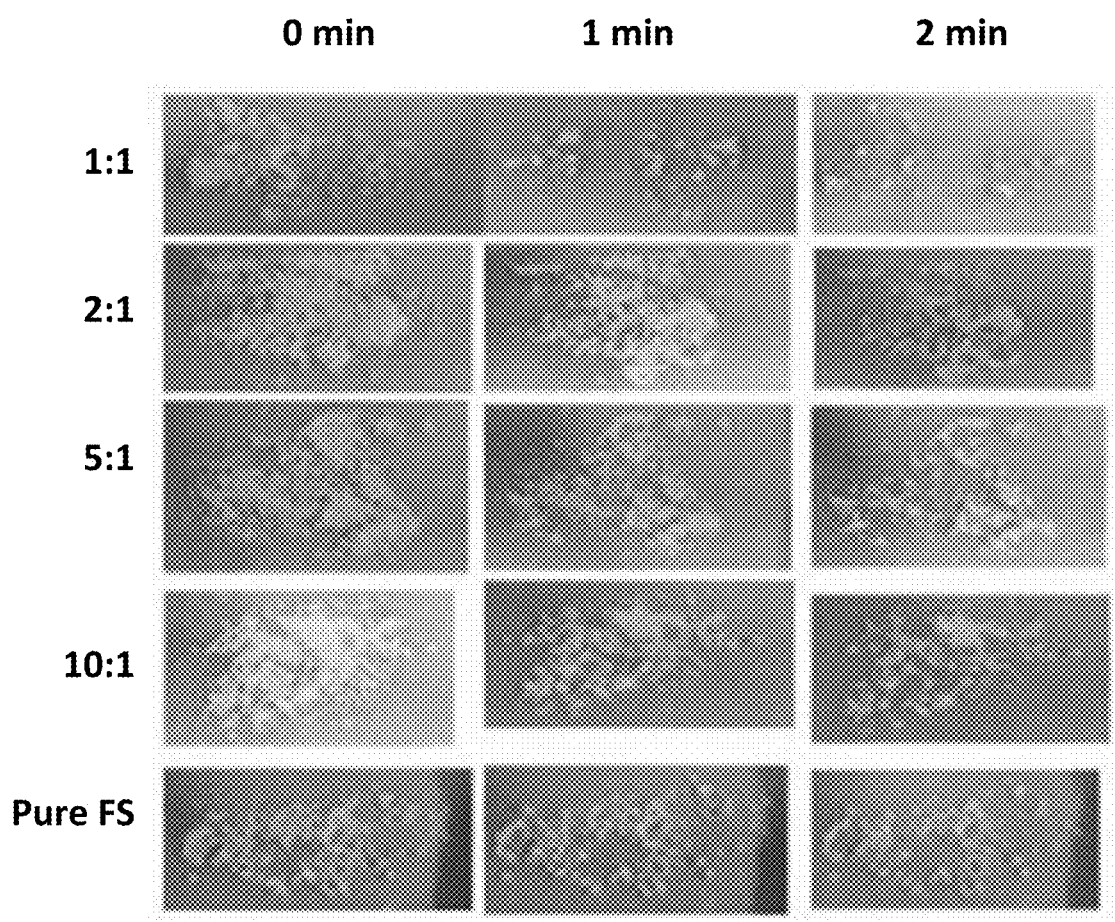
FIG. 5 is a composite photo showing the results of solubilization testing of the comparative compositions.

Referring now to FIG. 5, a composite image is shown representing the results of testing of the comparative mechanically mixed composition prepared by manually shaking dry powders in a container. The images taken at 0, 1, and 2 min for FS/ORC ratios—1:1; 2:1; 5:1; 10:1 as well as for FS powder with no ORC. The results indicate poor solubilisation even at 2 min time point for the comparative examples.

Figure 6:
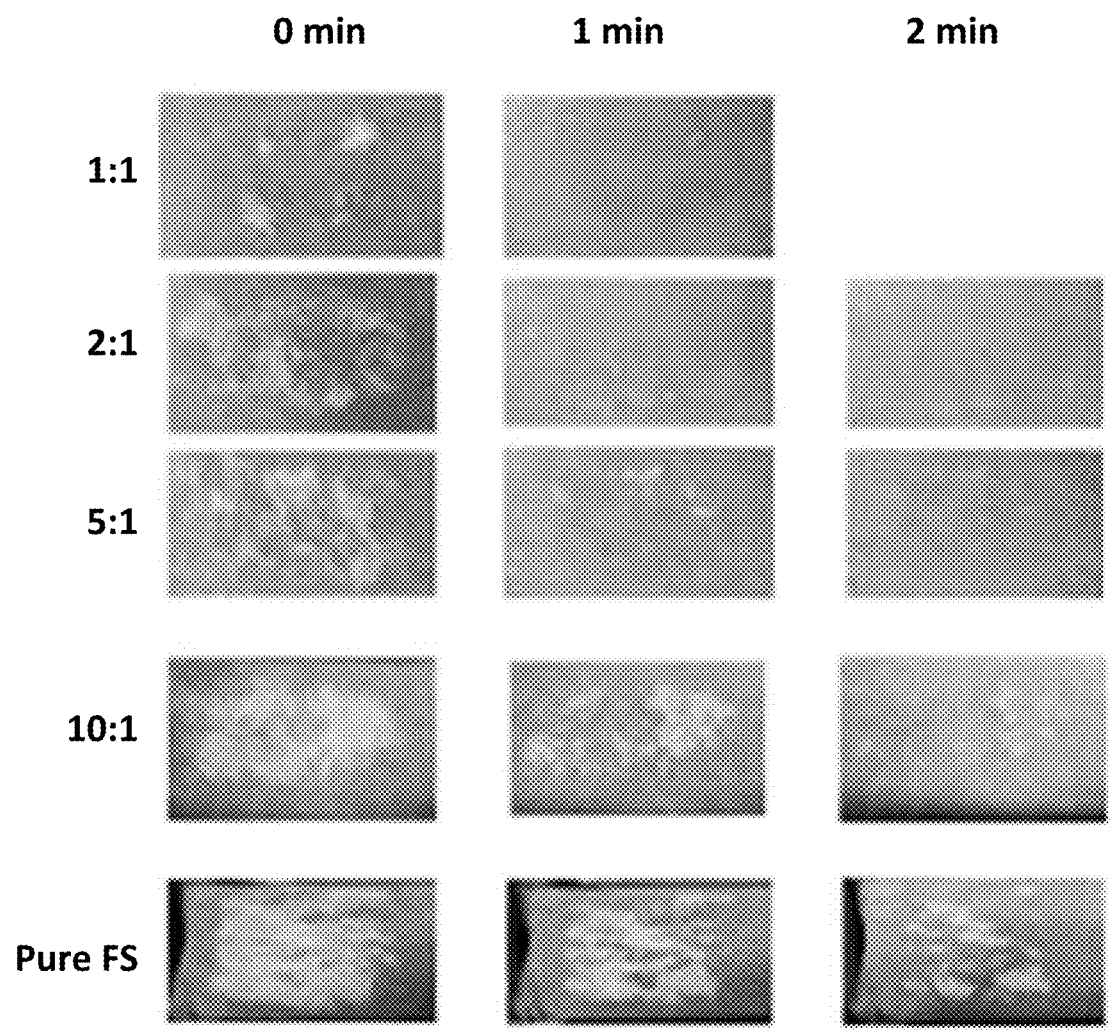
FIG. 6 is a composite photo showing the results of solubilization testing of the inventive compositions.

Referring now to FIG. 6, a composite image is shown representing the results of testing of the inventive hemostatic composition prepared by the spray method. The images taken at 0, 1, and 2 min for FS/ORC ratios—1:1; 2:1; 5:1; 10:1 as well as for FS powder with no ORC. The results indicate good solubilisation even at 1 min time point and very good solubilisation at 2 min time point, with rapid full solubilisation observed for 1:1 and 2:1 ratios already at 1 min and good solubilisation observed for all ratios at 2 min. Pure FS is showing poor solubilisation even at 2 min time point for the comparative example.

Figure 7:
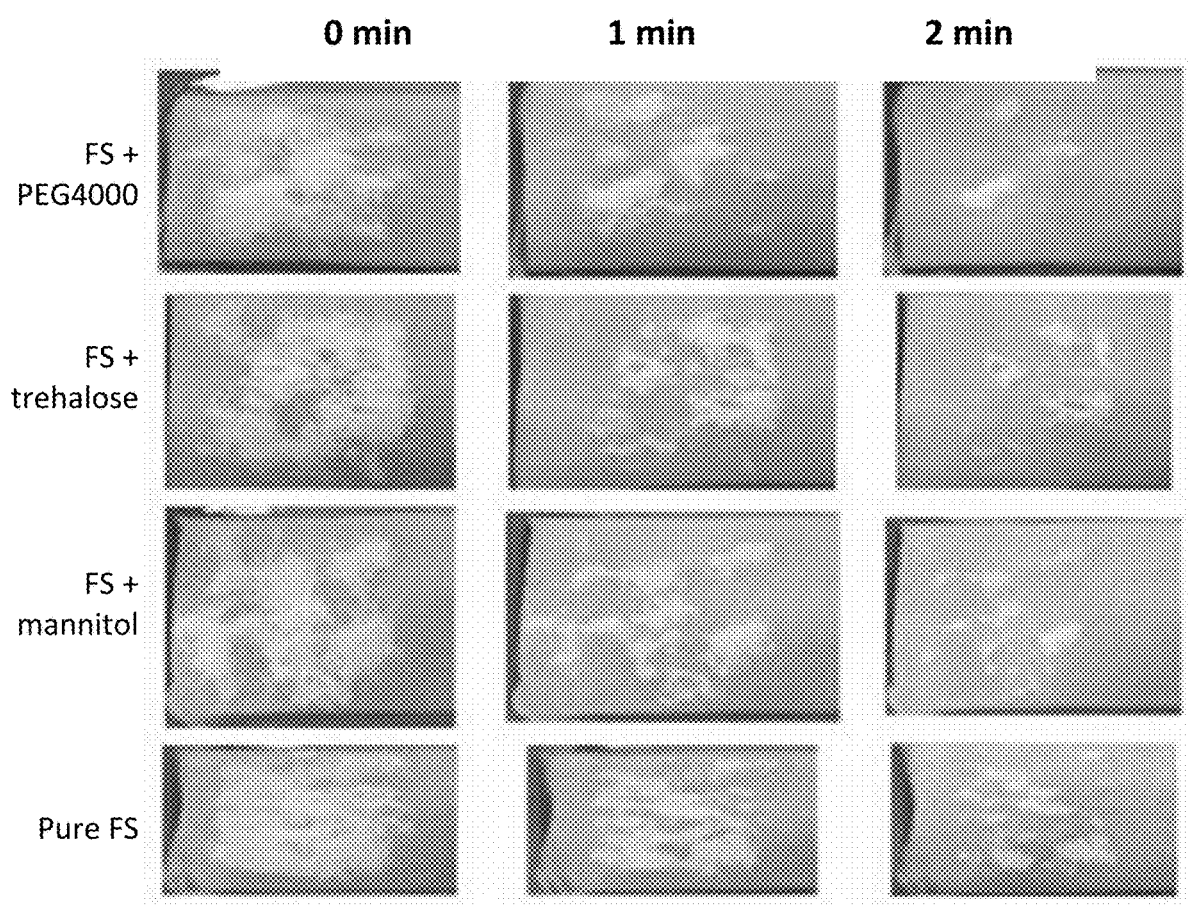
FIG. 7 is a composite photo showing the results of solubilization testing of the comparative compositions.

Referring now to FIG. 7, a composite image is shown representing the results of testing of the comparative compositions comprising FS with excipients added to fibrin sealant powder instead of ORC as well as for FS powder with no ORC. The excipients were Trehalose, PEG4000, Mannitol. Fibrin sealant powder mixtures with Trehalose, PEG 4000, Mannitol, were prepared by spray method as described above in 10:1 FS/excipient ratio. The images taken at 0, 1, and 2 min are shown. The results indicate poor solubilisation even at 2 min time point for the comparative examples.

The solubility of inventive hemostatic composition prepared by the spray method was affected by the concentration of the ORC component. Even at low concentrations of ORC, the solubility of the composition has improved.

Example 5. Particle Size Effects

The effects of the particle size on the performance of the inventive hemostatic compositions were evaluated. Particle size was controlled by sequentially passing the composition through sieves with apertures of 850 µm, 355 µm and 250 µm. Inventive composition powders were separated into size groups of predominantly above 850 µm, predominantly 355-850 µm, predominantly 250-355 µm and predominantly below 250 µm. Inventive hemostatic compositions made with 5:1 FS/ORC ratio were tested for solubility.

Figure 8:
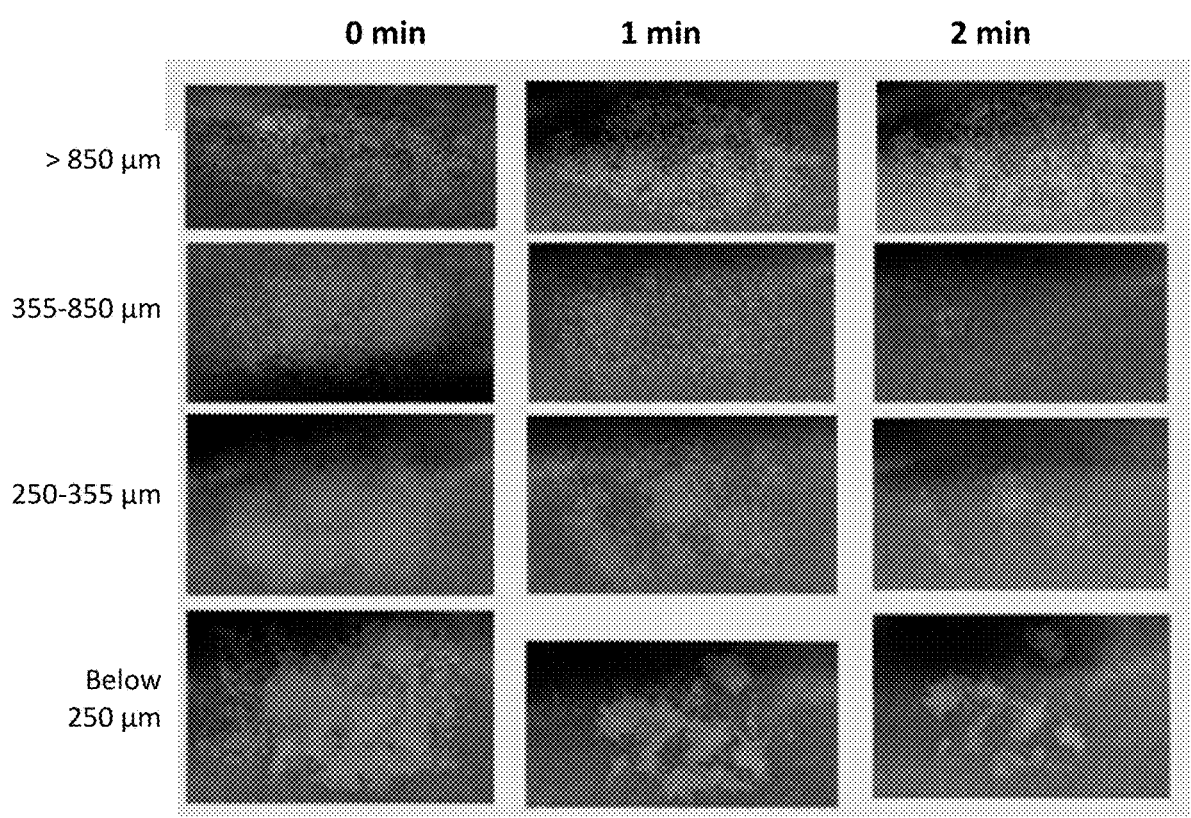
FIG. 8 is a composite photo showing the results of solubilization testing of the inventive compositions at varying particle size.

Referring now to FIG. 8, a composite image is shown representing the results of testing of the inventive hemostatic composition prepared by the spray method. The images taken at 0, 1, and 2 min for different powder size ranges. The results indicate particularly excellent solubilisation at 2 min point for predominantly 355-850 µm and good solubilisation for predominantly 250-355 µm compositions, with less effective solubilisation for compositions predominantly above 850 µm, and predominantly below 250 µm. Thus, the range of predominantly 250-850 µm is showing good solubilisation and is the preferred range for particle size, with particles predominantly in the 355-850 µm range particularly preferred. The resulting powder is an agglomerate of fibrinogen, thrombin, and ORC, and has many particles with size larger than the starting materials particle size.

Example 6. Effects of Tris Addition

A peel test of the inventive compositions with added Tris and without added Tris was performed. Tris additions were titrated to achieve pH=7. Tris powder was ground and passed through a 150 µm sieve. The powder of below 150 µm was collected and added the pre-determined amount into the dry mixture to adjust the pH of the composition, prior to co-spray.

The peel test was performed as follows. 0.5 g of the Inventive composition was applied to the corium tissue, covered by a composite bi-layer matrix which was pressed into the powder for 3 minutes, the sample-from-tissue separation force was measured by an Instron tensile testing machine and recorded as force per unit width (N/m). The composite bi-layer matrix comprised a layer of synthetic absorbable poly (glycolide-co-lactide) (PGL, 90/10 mol/mol) nonwoven fabric needlepunched into a knitted carboxylic-oxidized regenerated cellulose fabric (ORC), as described in U.S. Pat. No. 7,666,803 by D. Shetty et al., titled "Reinforced absorbable multilayered fabric for use in medical devices", which is incorporated by reference herein.

Referring now to Table NN, adhesion forces of inventive formulations are shown as a function of ORC addition. While the adhesion is lower at higher ORC content even 1:1 FS powder: ORC fiber formulation has appreciable peel force.

Referring now to Table 4, adhesion Forces of inventive formulations with and without Tris are shown for different FS/ORC ratios along with corresponding pH values. Tris was added in weight percentages listed to adjust pH to 7.0. While all compositions have exhibited high peel forces, presence of Tris clearly resulted in higher peel forces for the same FS/ORC ratios, with some showing 2-4 times higher peel force.

TABLE 4

Adhesion Forces of inventive formulations with and without Tris

| Composition FS/ORC ratio | With no Tris added | | With Tris added | | |
|---|---|---|---|---|---|
| | Peel Force N/m | pH | Peel Force N/m | pH | Tris % by weight |
| 1:1 | 26.7 | 2 | 72.6 | 7 | 20 |
| 2:1 | 53.8 | 2 | 127.5 | 7 | 14.3 |
| 5:1 | 41.2 | 5 | 235.9 | 7 | 7.7 |
| 10:1 | 221.7 | 5.5 | >340 (Above the upper limit of measurement) | 7 | 4.4 |

The analysis of data indicates surprising improvements in adhesive force or peel force for inventive composition having neutral pH achieved by Tris addition. While the force is somewhat lower Example 7. Characterization of Particles Referring now to FIG. 9, showing magnified SEM images of 5:1 FS/ORC inventive composition, it is apparent that the components of the composition are at least partially integrated, i.e. attached to each other or coated onto one another, and are not in a simple mechanical mixture.

Examination of the inventive composition in powder form shows the components well mixed and the biologics were closely attached on the ORC fibers.

Example 8. Hemostasis Testing

An in vivo test of hemostatic efficacy in liver abrasion model using the inventive hemostatic compositions was performed as follows. A liver abrasion model was created by creating an oozing area of 3 cm×3 cm on the surface of the porcine liver. 0.5 g of the inventive hemostatic composition having FS/ORC ratio of 5:1 was applied to cover the oozing area without any tamponade applied. Hemostasis was achieved in under 2 min.

An in vivo test of hemostatic efficacy in liver resection model using the inventive hemostatic compositions was performed as follows. A liver resection model was created by using the Pringle maneuver which is a surgical maneuver used in some abdominal operations whereby a large atraumatic hemostat is applied as a clamp. The Pringle maneuver was applied to control bleeding first, then a cut 5 cm long and 5 cm wide of the liver tissue was created along the liver edge to expose bile duct. Immediately after, the inventive hemostatic composition powder was applied to cover the transection plane, spraying saline simultaneously until bleeding was stopped. The Pringle clamp was then released to examine the results. It was observed that hemostasis was achieved and bile leak was prevented after the Pringle clamp was released. The hemostasis was achieved in 2 min.

Example 9. Method of Manufacturing in High Shear Reactor

According to an embodiment of the present invention, a process of making powdered hemostatic product comprises the steps of mixing the individual components as powders with HFE, creating a suspension in HFE (volatile non-aqueous solvent) in High Shear mixing/shearing reactor, having a low speed mixing blade and high-speed shear blade. As mixing is performed, HFE can evaporate through air seals of mixing blades and/or vacuum tube. A small amount of water is introduced into the reactor to aid particles binding/aggregation/clumping. The amount of water is sufficient for a small portion of the biologics to react and form particles, however it is not sufficient for all biologics i.e. thrombin and fibrinogen to fully react so that all fibrinogen is converted into fibrin. The portion of fibrinogen converted into fibrin is from about 0.1% to about 50%, more preferably 1% to 25%, even more preferably 2% to 10%. There is always an amount of clottable fibrinogen contained in the hemostatic powders prepared according to the present invention, available for reaction when powder is used on or in a wound.

According to an embodiment of the present invention, a method of making hemostatic powder, comprising the steps of: Forming a suspension of ORC powder, thrombin, fibrinogen, lysine, calcium salt in HFE (volatile non-aqueous solvent), agitating the suspension with high speed shear blade (and optionally continuously mixing the components simultaneously with a low speed mixer); Adding a small amount of water to the reactor to aid particles binding/aggregation/clumping; allowing HFE to evaporate from the reactor completely; Thus forming the hemostatic powder.

Referring to FIG. 10, a schematic block-diagram of the process of making the hemostatic material according to the present invention is shown and comprises the steps of:
- Preparing dry powders mixture of fibrinogen, thrombin, ORC, optionally calcium chloride, and optionally buffer compound such as Tris and/or lysine;
- Suspending dry powders mixture in a non-aqueous solvent capable of rapid evaporation under ambient conditions in a High Shear Mixer reactor
- Agitating the suspension with high speed shear blade and optionally continuously mixing the components simultaneously with a low speed mixer blade
- Introducing a small amount of water into the reactor to aid particles binding/aggregation/clumping
- Allowing the non-aqueous solvent to evaporate from the reactor drying the resulting hemostatic material
- Removing the resulting hemostatic material from the reactor and optionally sieving, thus forming at least partially integrated ORC fibers, fibrinogen, and thrombin in a form of an aggregated powder In one embodiment, Lysine or Tris in a powder form is added to the fibrinogen, thrombin, and ORC mixture for pH adjustment.

According to one aspect of the present invention the inventive hemostatic material comprises substantially uniformly distributed at least partially integrated ORC fibers, fibrinogen, and thrombin in a form of a powder According to one aspect of the present invention, the inventive hemostatic material has high uniformity, integration, fast gelling/clotting, and strong adhesion force.

Figure 11:
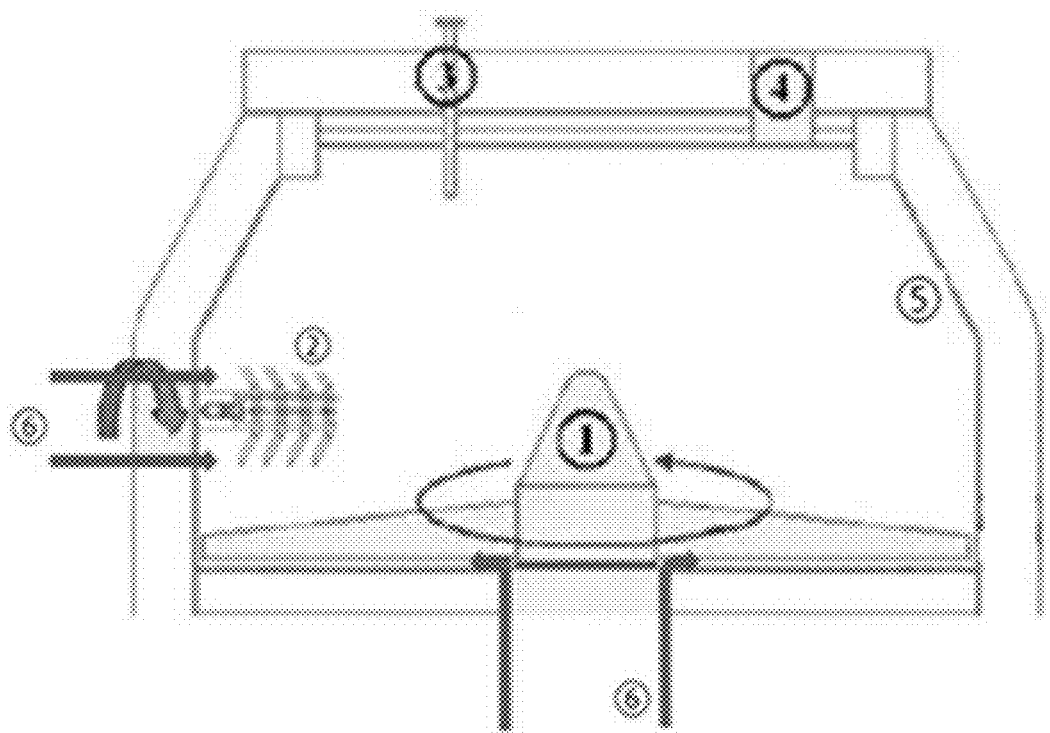
FIG. 11 is a schematic diagram of the HSM manufacturing reactor.

Referring now to FIG. 11, a schematic rendering of a High Shear mixing (HSM) reactor is shown, with container or bowl 5, Impeller 1 for the raw materials mixing and suspending (low speed mixer); High speed shearing blade or chopper knife 2; Spray nozzle 3 for the water (binder) additions; Vent 4 for the removal of HFE volatile fluid; Pathways 6 for ingress of optional air or gas for purging HFE volatile fluid through mixing and/or shearing blades seals. Alternatively, a dedicated air intake can be provided (no shown). Alternatively, a vacuum can be connected to vent 4.

HSM reactors are available commercially. The reactor used in the present examples was HSM model Mini-CG, available from Chuangzhi Electrical and Mechanical Co., Ltd. (China).

Example 10. Comparative Testing of Hemostatic Powders Made by Spray Methods of Example 1 and HSM Methods of Example 9

The inventors compared the HSM method (Example 9) particles vs. particles made by spraying through a nozzle of HFE suspension (Example 1). The test results showed the hemostatic powders made by the HSM method had comparable physiochemical properties and functional performance like tensile strength and adhesion strength, and had comparable hemostatic efficacy in animal study to the powders made by the spaying method of Example 1.

Comparison of powders of Example 1 formulated with Tris buffer to powders formulated in Example 9 (HSM method) using Lysine as buffering compound showed no substantial difference in hemostatic powder performance.

Advantageously, HSM method of preparing hemostatic powder granulations has advantages of providing HSM equipment that is a substantially sealed system so that powder can be granulated in a sealed environment, and no material is lost during the process. The bioburden could be minimized as compared to spraying method of Example 1.

Figure 12:
FIG. 12 shows inventive hemostatic powder prepared by the HSM Method of Example 9.

Referring to FIG. 12, a hemostatic powder prepared by the HSM Method of Example 9 is shown.

Figure 13:
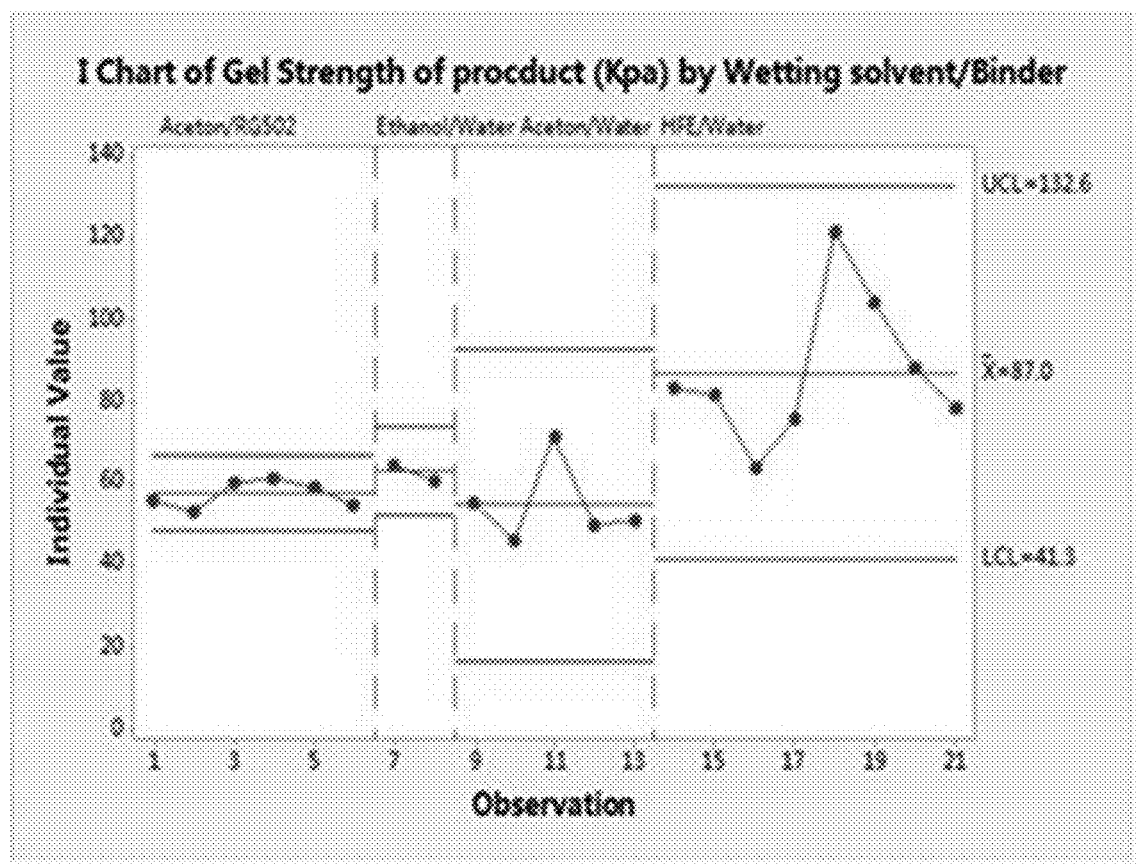
FIG. 13 shows a Chart of gel strength in kPa.
Figure 15:
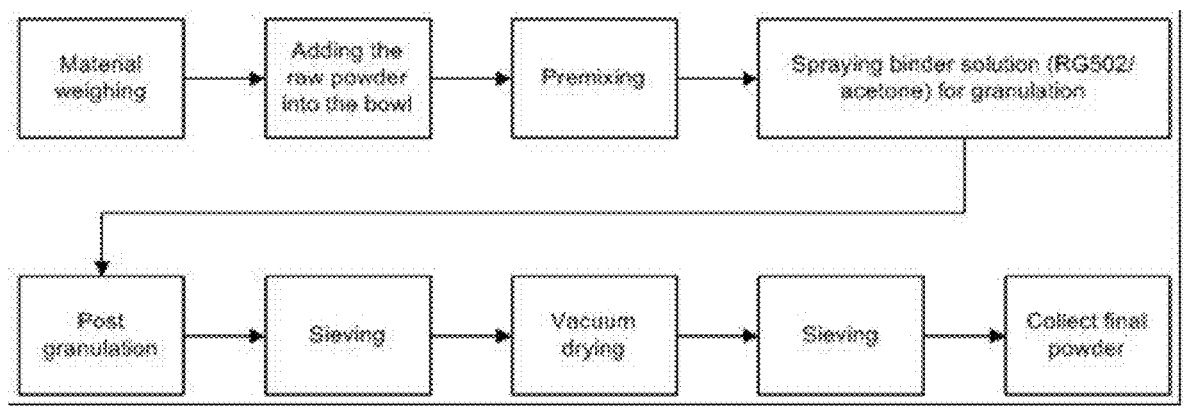
FIG. 15 shows schematic block-diagram of the HSM manufacturing process for preparation of hemostatic powders using acetone and polymer RG502.

Example 11. Preparation of Hemostatic Compositions Using HSM Method: Comparison of Various Solvents/Binders The inventors used the HSM method (Example 9) to manufacture hemostatic powders using several different solvents/binders. Referring to FIG. 13, a Chart of gel strength in kPa is shown, with the gel formed by the hemostatic powders of the present invention, whereby such powders were made by using one of four different solvents and/or binders. The gel strength is shown for several different testing points. First segment of the chart shows gel strength for acetone as a volatile suspension solvent and polymer RG502 (D, L-lactide-co-glycolide) as a binder. The second segment shows gel strength for ethanol/water combination as volatile solvent and binder. The third segment shows gel strength for acetone/water combination as volatile solvent and binder. The fourth segment shows gel strength for HFE/water combination as volatile solvent and binder. As can be seen from Chart of FIG. 13, HFE/water combination shows the highest gel strength.

Referring now to FIG. 14, the results of testing in animal models of the hemostatic powders made by using different solvents/binders are presented (Hemostasis testing on dermatome liver surface model). As can be seen from the FIG. 14, combinations of acetone/RG502; ethanol/water; acetone/water all showing bleeding after 3 min after application. To the contrary, the inventive HFE/water combination shows cessation of bleeding after only 1 minute.

Example 12. Preparation of Hemostatic Compositions Using HSM Method and Polymer RG502/Acetone 200 g of raw material powder including Fibrinogen powder/Thrombin powder/ORC powder/Calcium chloride powder and Tris was prepared according to the formulation shown in Table 5. The binder/suspension solution was prepared from 74.7 g acetone and 8.3 g polymer RG502(D,L-lactide-co-glycolide), with polymer fully dissolved and mixed thoroughly.

TABLE 5

| \multicolumn{3}{c}{Formulation for Example 12} |||
|---|---|---|
| Raw material | Fibrinogen (g) | 153.54 |
|  | Thrombin (g) | 15.08 |
|  | Calcium chloride (g) | 5.24 |
|  | ORC (g) | 17.40 |
|  | Tris (g) | 8.70 |
| Binder | Polymer RG502 (g) D,L-lactide-co-glycolide | 8.30 |
|  | Acetone (g) | 74.70 |

Figure 16:
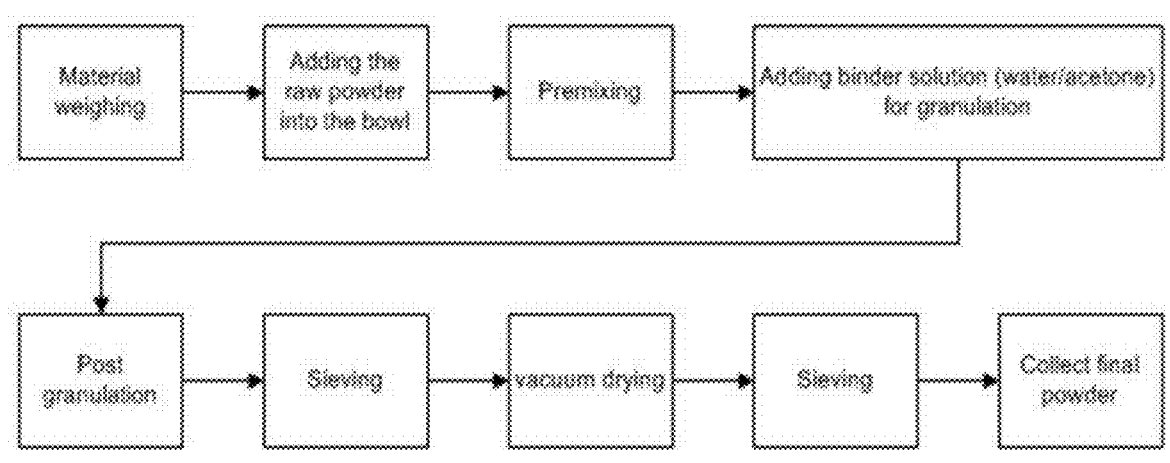
FIG. 16 shows schematic block-diagram of the HSM manufacturing process for preparation of hemostatic powders using acetone and water.
Figure 17:
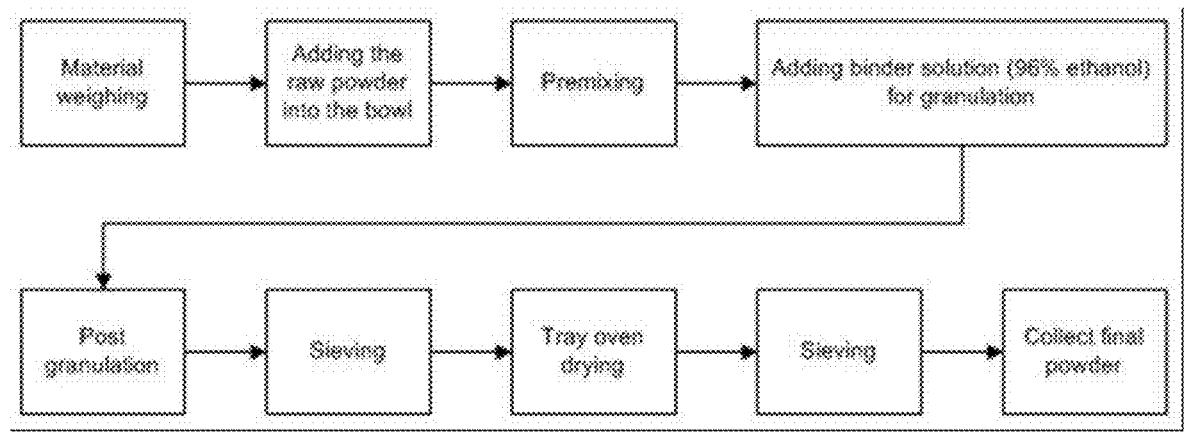
FIG. 17 shows schematic block-diagram of the HSM manufacturing process for preparation of hemostatic powders using 96% ethanol.

The schematic block-diagram of the manufacturing process is shown in FIG. 16. All dry material was transferred into the bowl of HSM, premixed for 5 minutes using the mixing blade impeller speed at 75 rpm, high shear blade chopper speed at 1000 rpm. The binder/suspension solution (RG502/acetone) was then sprayed onto the dry materials by a Peristaltic pump and a spray nozzle, with the feed flowrate 60 g/min. The solution of polymer/acetone starts binding the raw material particles to form powder.

The Impeller speed was then increased to 150 rpm and the chopper speed increased to 3000 rpm, continuing the post granulation process for 5 mins.

After granulation, a sieve (the pore size is 1.7 mm) was used to sieve the materials and collect the resulting powder under the sieve. The powder was transferred to vacuum drying box and dried for 1 hour. Two sieves (pore size 106 and 425 μm) were then used to sieve the product. The final powder fraction was collected between the two sieves.

Example 13. Preparation of Hemostatic Compositions Using HSM Method and Water/Acetone 200 g of raw material powder including Fibrinogen powder/Thrombin powder/ORC powder/Calcium chloride powder and Tris was prepared according to the formulation shown in Table 6. The binder/suspension solution was prepared from 68 g acetone and 17 g of purified water, mixed thoroughly.

TABLE 6

| \multicolumn{3}{c}{Formulation for Example 13} |||
|---|---|---|
| Raw material | Fibrinogen (g) | 153.54 |
|  | Thrombin (g) | 15.08 |
|  | Calcium chloride (g) | 5.24 |
|  | ORC (g) | 17.40 |
|  | Tris (g) | 8.70 |
| Binder | Water (g) | 17.00 |
|  | Acetone (g) | 68.00 |

Figure 18:
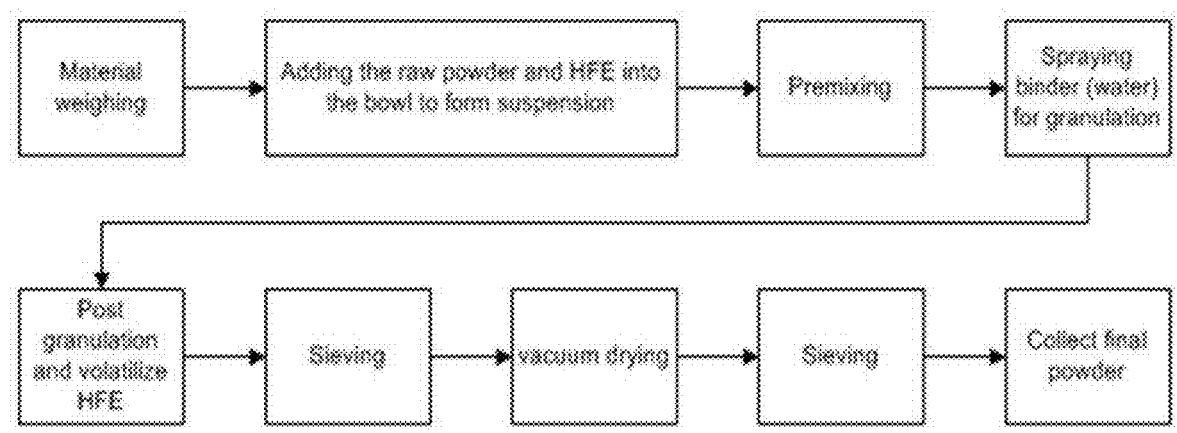
FIG. 18 shows schematic block-diagram of the HSM manufacturing process for preparation of hemostatic powders using HFE/water.

The schematic block-diagram of the manufacturing process is shown in FIG. 18. All dry material was transferred into the bowl of HSM, premixed for 5 minutes using the mixing blade impeller speed at 75 rpm, high shear blade chopper speed at 1000 rpm. The binder/suspension solution (water/acetone) was then sprayed onto the dry materials by a Peristaltic pump and a spray nozzle, with the feed flowrate 60 g/min. The solution starts binding the raw material particles to form powder.

The Impeller speed was then increased to 120 rpm and the chopper speed increased to 3000 rpm, continuing the post granulation process for 3 mins.

After granulation, a sieve (the pore size is 1.7 mm) was used to sieve the materials and collect the resulting powder under the sieve. The powder was transferred to vacuum drying box and dried for 1 hour under vacuum. Two sieves (pore size 106 and 425 μm) were then used to sieve the product. The final powder fraction was collected between the two sieves Example 14. Preparation of Hemostatic Compositions Using HSM Method and 96% Ethanol 150 g of raw material powder including Fibrinogen powder/Thrombin powder/ORC powder/Calcium chloride powder and Tris was prepared according to the formulation shown in Table 7. The binder/suspension solution was prepared from 60 g of 96% ethanol.

TABLE 7

| \multicolumn{3}{c}{Formulation for Example 14} |||
|---|---|---|
| Raw material | Fibrinogen (g) | 115.16 |
|  | Thrombin (g) | 11.31 |
|  | Calcium chloride (g) | 3.93 |
|  | ORC (g) | 13.05 |
|  | Tris (g) | 6.53 |
| Binder | 96% Ethanol (g) | 60.00 |

Figure 20:
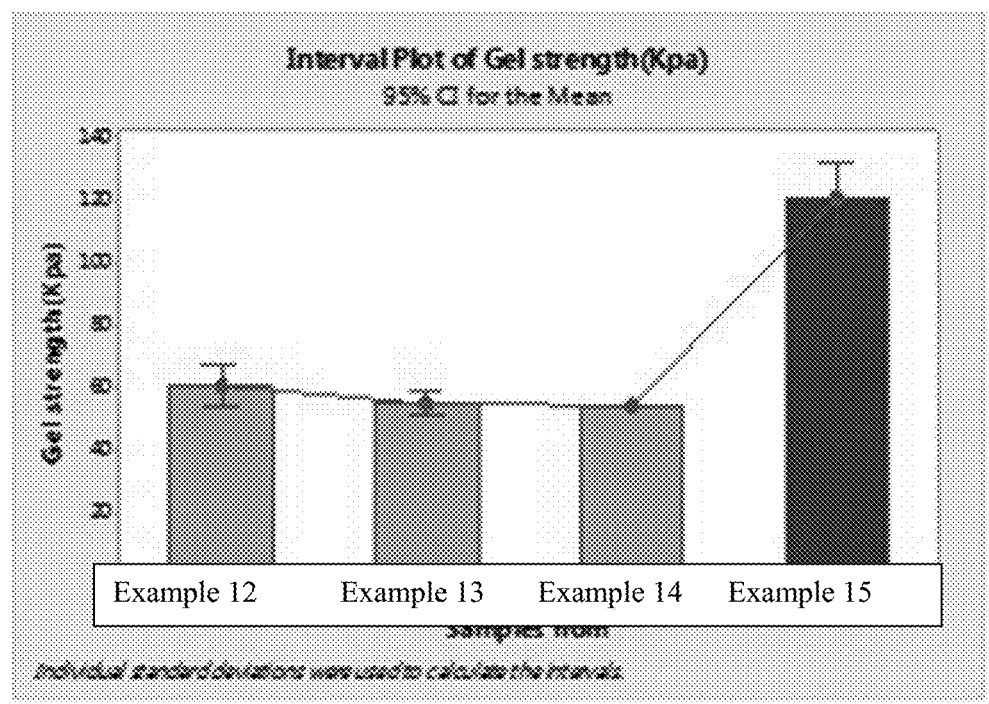
FIG. 20 shows gel strength properties of hemostatic powders obtained with various solvents/binders.

The schematic block-diagram of the manufacturing process is shown in FIG. 20. All dry material was transferred into the bowl of HSM, premixed for 3 minutes using the mixing blade impeller speed at 75 rpm, high shear blade chopper speed at 1000 rpm. The binder/suspension solution (96% ethanol) was then sprayed onto the dry materials by a Peristaltic pump and a spray nozzle, with the feed flowrate 4 g/min. The solution starts binding the raw material particles to form powder.

The Impeller speed was then increased to 120 rpm and the chopper speed increased to 1500 rpm, continuing the post granulation process for 3 mins.

After granulation, a sieve (the pore size 710 μm) was used to sieve the materials and collect the resulting powder under the sieve. The powder was transferred to tray oven for drying and dried at 45° C. for 0.5 hr.

Two sieves (pore size 100 and 315 μm) were then used to sieve the product. The final powder fraction was collected between the two sieves Example 15. Preparation of Hemostatic Compositions Using HSM Method and HFE/Water 100 g of raw material powder including Fibrinogen powder/Thrombin powder/ORC powder/Calcium chloride powder and Tris was prepared according to the formulation shown in Table 8. 500 g of HFE7100 was utilized.

TABLE 8

| Formulation for Example 15 | | |
|---|---|---|
| Raw material | Fibrinogen (g) | 76.77 |
| | Thrombin (g) | 7.54 |
| | Calcium chloride (g) | 2.62 |
| | ORC (g) | 8.70 |
| | Tris (g) | 4.35 |
| Suspending agent | HFE 7100 (g) | 500.00 |
| Binder | Water (g) | 9.00 |

Figure 22:
FIG. 22 shows the inventive hemostatic powder forming a gel (counted for 2 min) on the deflated lung.

The schematic block-diagram of the manufacturing process is shown in FIG. 22. All dry material was transferred into the bowl of HSM and 500 g of HFE7100 added. The composition was premixed for 3 minutes to form a suspension, using the mixing blade impeller speed at 200 rpm. 9 g of water was then sprayed into the suspension by a Peristaltic pump and a spray nozzle, with the feed flowrate of 4.5 g/min. The solution starts binding the raw material particles to form powder.

The Impeller speed was then adjusted to 100-300 rpm and the chopper speed set at 150-1000 rpm, continuing the granulation process for 10 mins. Sealing pressure of impeller and chopper was adjusted to 0.02 MPa to blow off HFE and dry the composition.

After granulation, a sieve (the pore size 710 µm) was used to sieve the materials and collect the resulting powder under the sieve. The powder was transferred vacuum box for drying and dried for 12-24 hours at vacuum from 0-10 Pa.

Two sieves (pore size 106 and 355 µm) were then used to sieve the product. The final powder fraction was collected between the two sieves.

Example 16. Comparison of Hemostatic Powder Formulations Obtained in Examples 12, 13, 14, 15

Figure 19:
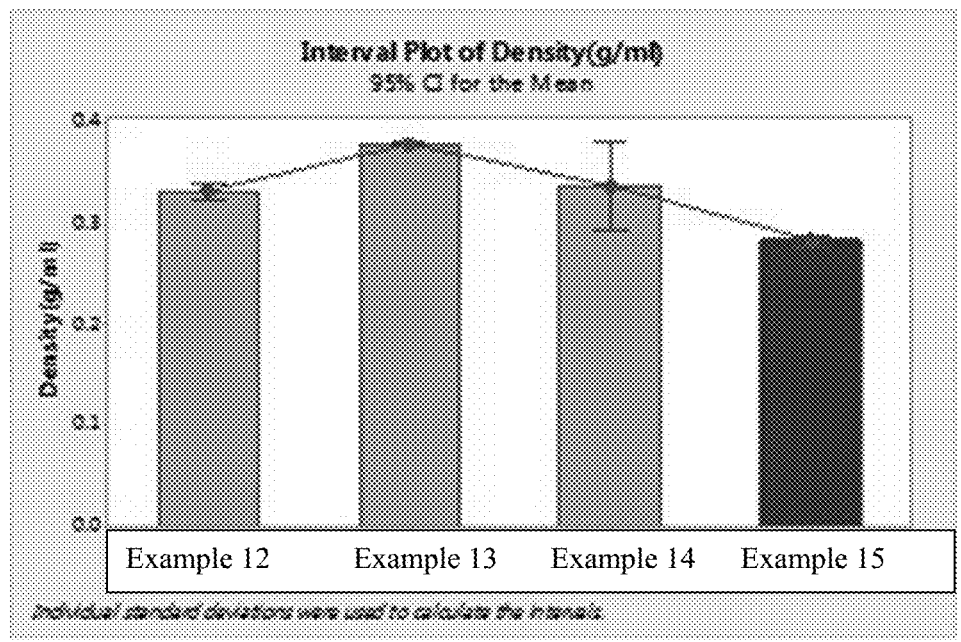
FIG. 19 shows density properties of hemostatic powders obtained with various solvents/binders.

Hemostatic powders obtained as described in Examples 12, 13, 14, 15 were compared for their performance. Water content was tested by Karl Fischer method; Thrombin potency was tested based on clotting time; Clottable protein was tested by quantifying fibrinogen; Particle size was tested by Laser particle size analyzer; Density was measured as Bulk density; Gel strength was measured as Tensile strength test. The results of the testing are shown in Table 9 and in FIGS. 19, 20.

TABLE 9

Properties of hemostatic powders obtained with various solvents/binders

| | Water content (%) | Thrombin potency (IU/mg) | Clottable Protein (mg/g) | Density (g/ml) | Particle size D50 (µm) | Gel strength (Kpa) |
|---|---|---|---|---|---|---|
| Example 12 | 2.32 | 1.78 | 290.11 | 0.33 | 181.97 | 61.13 |
| Example 13 | 2.44 | 2.19 | 324.55 | 0.38 | 201.57 | 55.35 |
| Example 14 | 3.87 | 2.03 | 284.08 | 0.34 | 71.98 | 55.00 |
| Example 15 | 2.80 | 1.80 | 326.76 | 0.29 | 57.66 | 121.15 |

Advantageously, the volatile properties of HFE potentially increase the porosity of final hemostatic powder product, which will lead to a decrease in the density of the final product, and speeds up the dissolution or re-dispersion time. The density of the powders of Example 15 is lowest, while the strength of formed gel is highest vs. other methods. The hemostatic performance was also better as was shown in FIG. 14.

Example 17. Testing of the Inventive Hemostatic Powder in Lung Sealing Model

Two studies were conducted to test the hemostatic powders of the present invention for sealing function on lung leak model. Both studies showed at 30 cm H2O pressure, the present powder formed gel that was tightly adhering to the lung tissue and sealed the leak very well. When the pressure was 40 cm H2O, the gel started to delaminate, but still could seal the leak.

Figure 21:
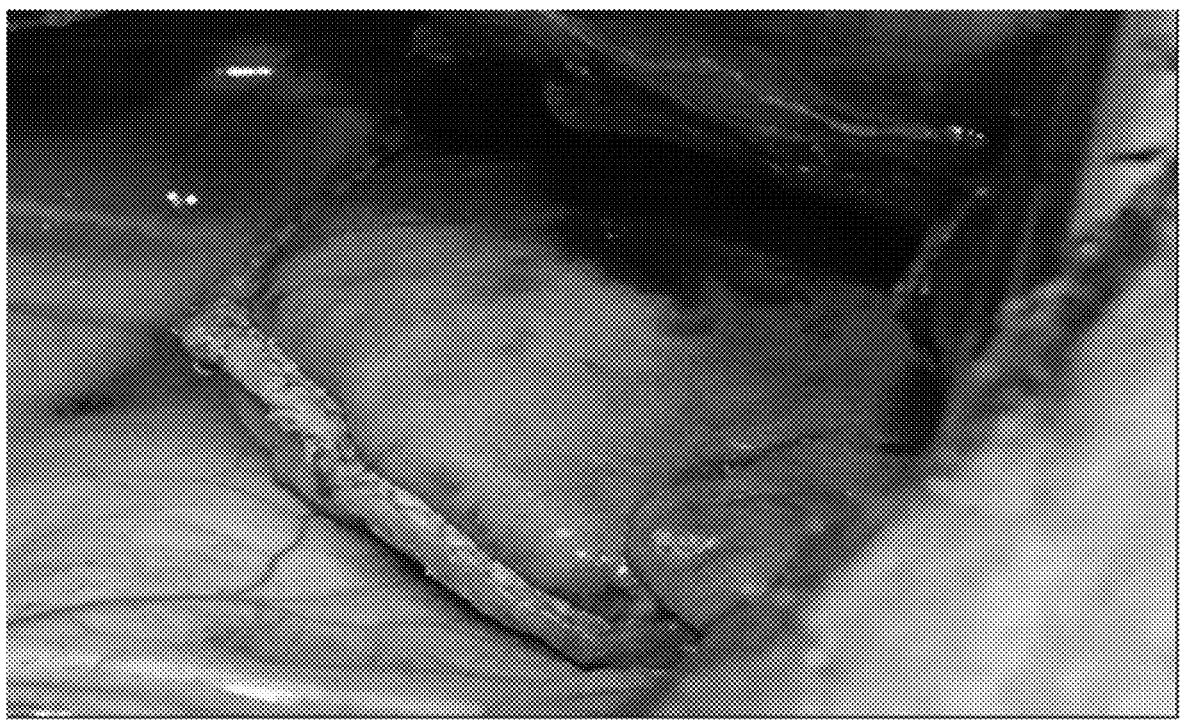
FIG. 21 shows Lung leak model with 1.2 cm long incision.
Figure 23:
FIG. 23 shows the inventive hemostatic powder forming a gel that seals the lung leak at 30 cm $H_2O$.
Figure 24:
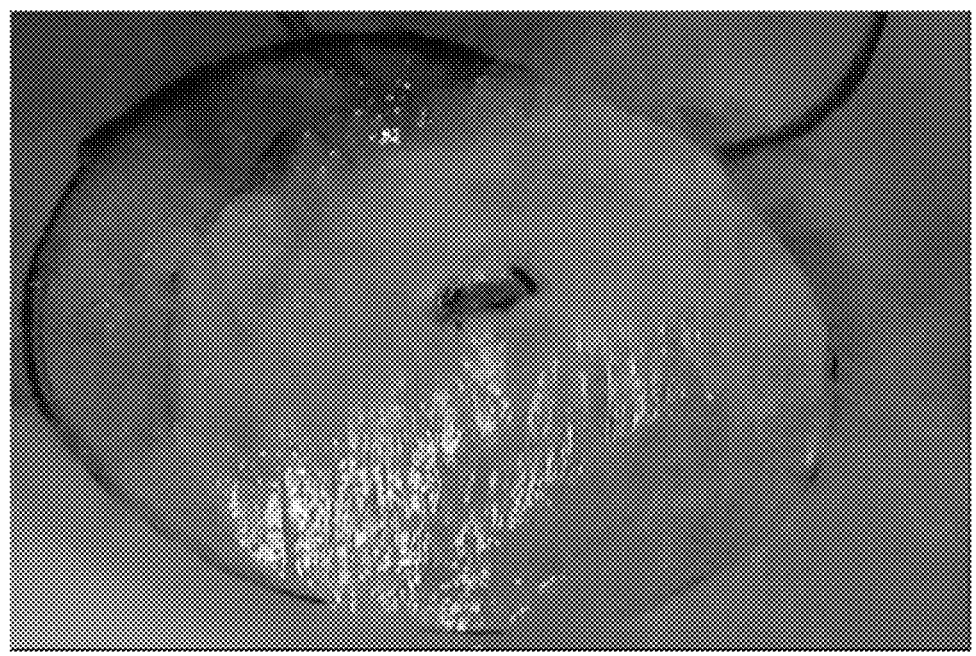
FIG. 24 shows Lung leak model with 1 cm long incision.
Figure 25:
FIG. 25 shows the inventive hemostatic powder forming a gel that seals the lung leak at 30 cm $H_2O$.
Figure 26:
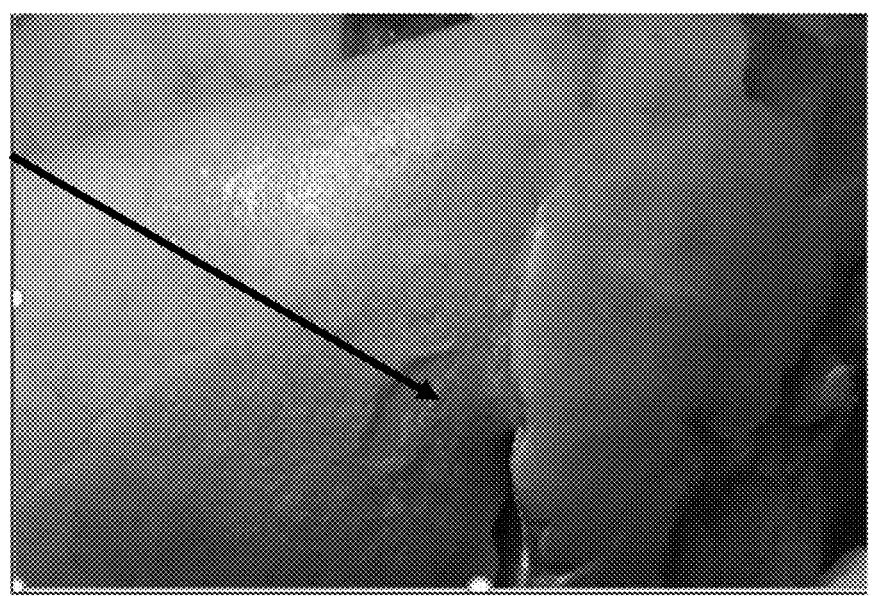
FIG. 26 shows the inventive hemostatic powder forming a gel partially delaminated at 40 cm $H_2O$ pressure (arrow indicates the delamination area).

FIG. 21 shows Lung leak model with 1.2 cm long incision;

FIG. 22 shows the inventive hemostatic powder forming a gel (counted for 2 min) on the deflated lung;

FIG. 23 shows the inventive hemostatic powder forming a gel that seals the lung leak at 30 cm H2O;

FIG. 24 shows Lung leak model with 1 cm long incision;

FIG. 25 shows the inventive hemostatic powder forming a gel that seals the lung leak at 30 cm H2O;

FIG. 26 shows the inventive hemostatic powder forming a gel partially delaminated at 40 cm H2O pressure (arrow indicates the delamination area).

Advantageously, the inventive hemostatic powder is shown to be able to seal lung leaks.

We claim:

1. A method of forming a powdered hemostatic composition, comprising the steps of:
   a) forming a suspension of a mixture comprising particles, the particles comprising fibrinogen, thrombin, oxidized regenerated cellulose (ORC) fibers, in a non-aqueous low boiling solvent comprising hydrofluoroether;
   b) agitating and shearing said suspension in a high shear mixing reactor;
   c) adding water in an amount of at least 9 g per 100 g of said particles, resulting in 0.1% to less than 25% of fibrinogen conversion into fibrin so as to form agglomerated particles comprising said fibrinogen, thrombin and ORC fibers, while preventing full clotting of the fibrinogen;
   d) allowing the non-aqueous solvent to evaporate;
   e) drying and sieving the composition; and thus forming the powdered hemostatic composition.

2. The method of claim 1, wherein said non-aqueous low boiling solvent comprises HFE7100.

3. The method of claim 1, wherein said suspension further comprises Lysine or Tris.

4. The method of claim 1, wherein said suspension further comprises calcium chloride.

5. The method of claim 1, wherein said water is added in an amount of 9 g per 100 g of said particles.

\* \* \* \* \*